(12) United States Patent
Meece

(10) Patent No.: US 8,850,905 B2
(45) Date of Patent: Oct. 7, 2014

(54) AUTOMATED SAMPLING OF DISSOLVED CONTAMINANTS IN WATER

(75) Inventor: Douglas A. Meece, West Chester, OH (US)

(73) Assignee: EST Analytical, Inc., Fairfield, OH (US)

( * ) Notice: Subject to any disclaimer, the term of this patent is extended or adjusted under 35 U.S.C. 154(b) by 453 days.

(21) Appl. No.: 13/414,970

(22) Filed: Mar. 8, 2012

(65) Prior Publication Data

US 2013/0233094 A1    Sep. 12, 2013

(51) Int. Cl.
*G01N 35/10* (2006.01)

(52) U.S. Cl.
USPC .................................................... 73/864.21

(58) Field of Classification Search
None
See application file for complete search history.

(56) References Cited

U.S. PATENT DOCUMENTS

| | | |
|---|---|---|
| 5,337,619 A | 8/1994 | Hodgins et al. |
| 5,441,700 A | 8/1995 | Markelov |
| 5,814,514 A * | 9/1998 | Steffan et al. ............... 435/262 |
| 5,827,944 A | 10/1998 | Nickerson |
| 5,866,072 A | 2/1999 | Bowe, Jr. et al. |
| 5,932,482 A | 8/1999 | Markelov |
| 6,146,895 A | 11/2000 | Green et al. |
| 6,277,649 B1 | 8/2001 | Markelov |
| 6,365,107 B1 | 4/2002 | Markelov et al. |
| 6,395,229 B1 | 5/2002 | Markelov |
| 6,395,560 B1 | 5/2002 | Markelov |
| 7,803,635 B1 | 9/2010 | Meece |
| 2004/0142481 A1 | 7/2004 | Hartlein ...................... 436/164 |

OTHER PUBLICATIONS

Technical Guidance for the Natural Attenuation Indicators: Methane, Ethane, and Ethene, Revision 1; US EPA-Region 1; Jul. 2001.
Methane, Ethene, and Ethane Headspace and Gas Chromatography, Rev.4.1; PA-DEP Bureau of Labs; before 2011.

* cited by examiner

*Primary Examiner* — Robert R Raevis
(74) *Attorney, Agent, or Firm* — Frederick H. Gribbell

(57) ABSTRACT

An automated sampler for sampling contaminants that are dissolved in water. An empty, sealed first vial is placed at a first sampling station with a dual-port needle, and a mechanical syringe pump displaces a programmable volume of gas from the first vial. A sealed second vial having a field sample of water with dissolved contaminants, typically without a headspace region, is placed at a second sampling station, with a dual-port needle. The syringe pump extracts an aqueous volume from the second vial, then transfers the aqueous volume into the first vial. This is all done without exposing the field sample to any external gasses or other compounds, and without opening the seal of the field sample to atmosphere. The sample in the first vial is heated, and an aliquot of headspace from the first vial is then injected into an analyzer device for identification and quantification.

21 Claims, 23 Drawing Sheets

PREVACUATION MODE

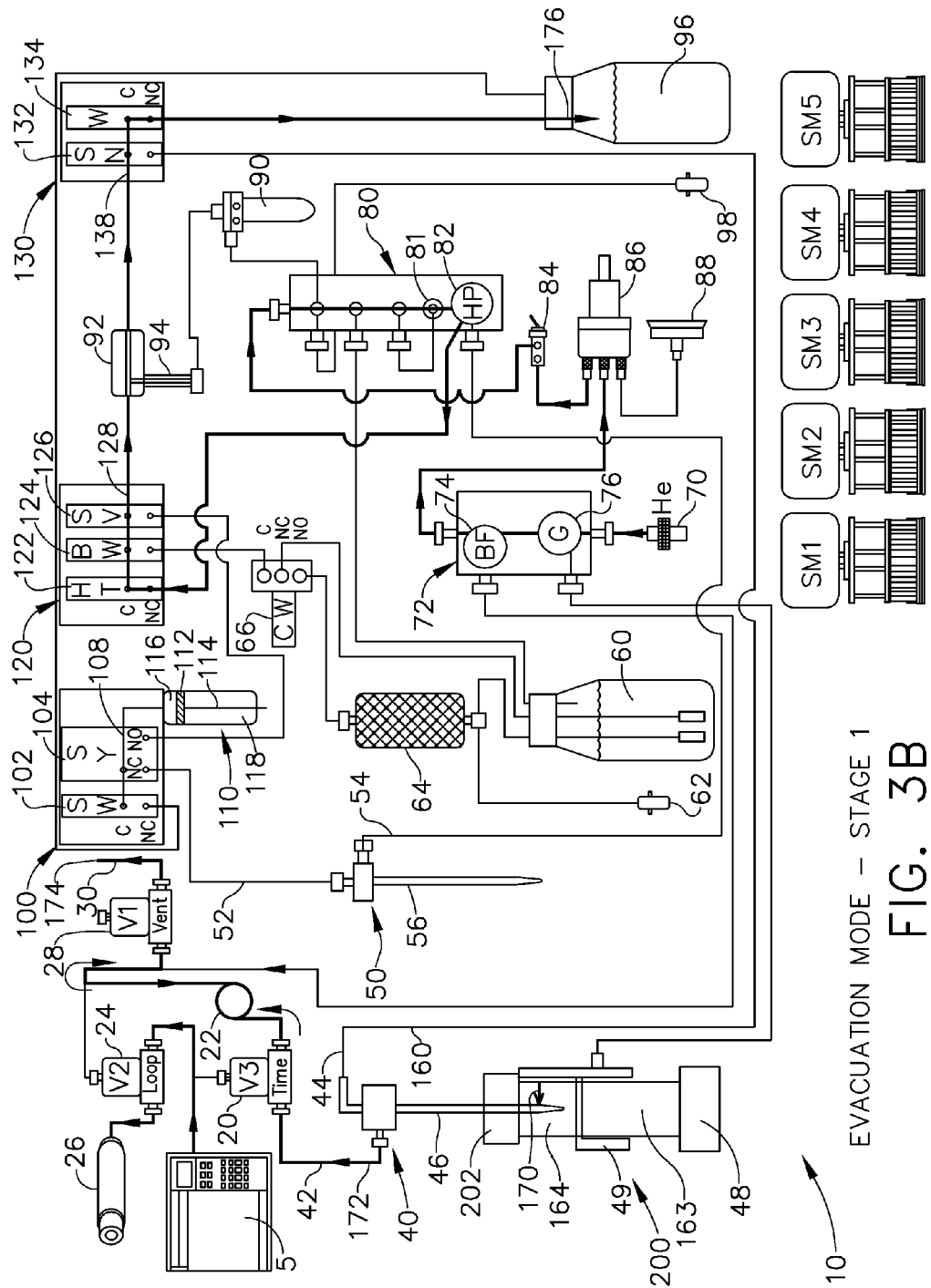
FIG. 3B  EVACUATION MODE – STAGE 1

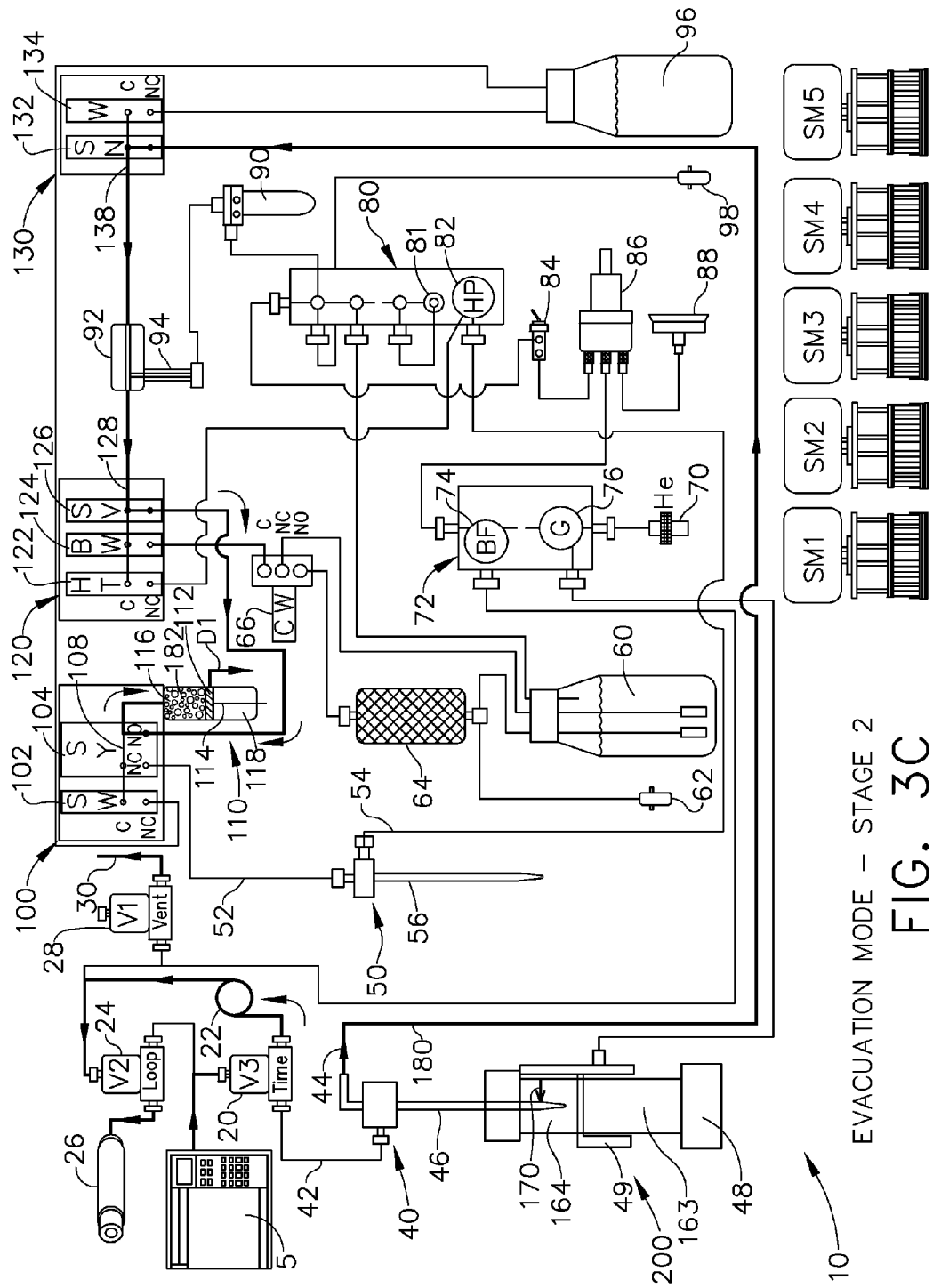
FIG. 3C  EVACUATION MODE – STAGE 2

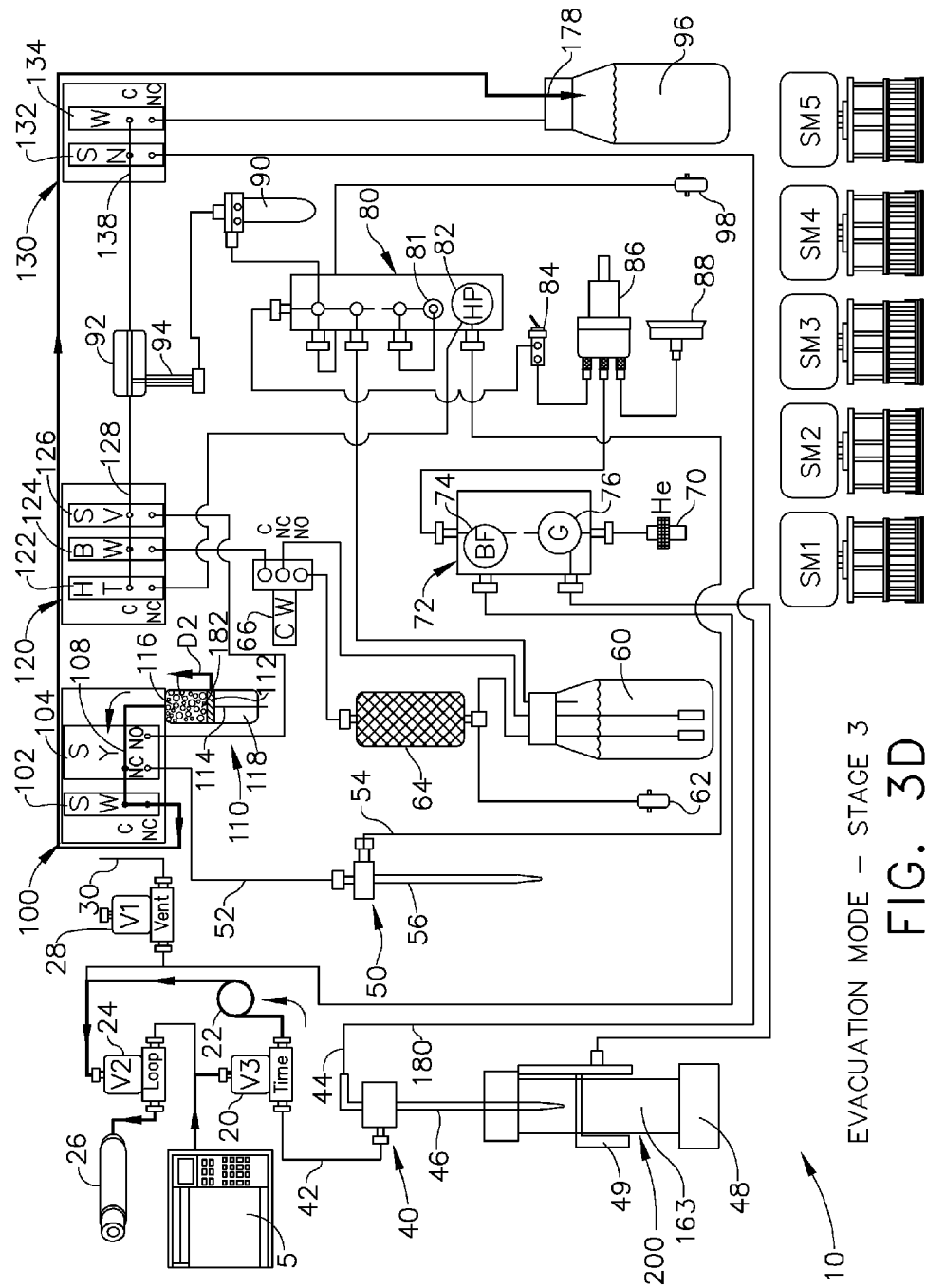
FIG. 3D — EVACUATION MODE — STAGE 3

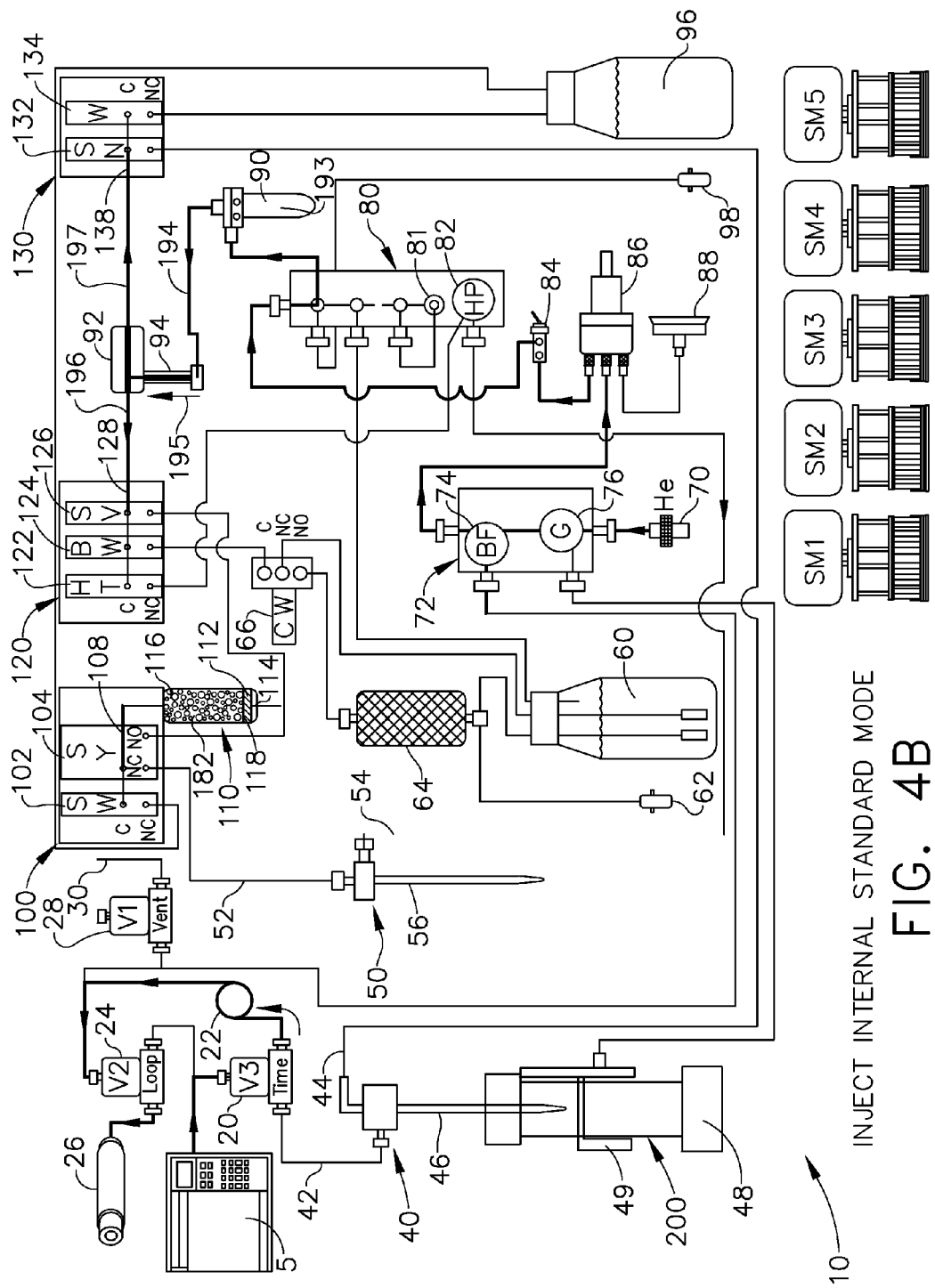
FIG. 4B  INJECT INTERNAL STANDARD MODE

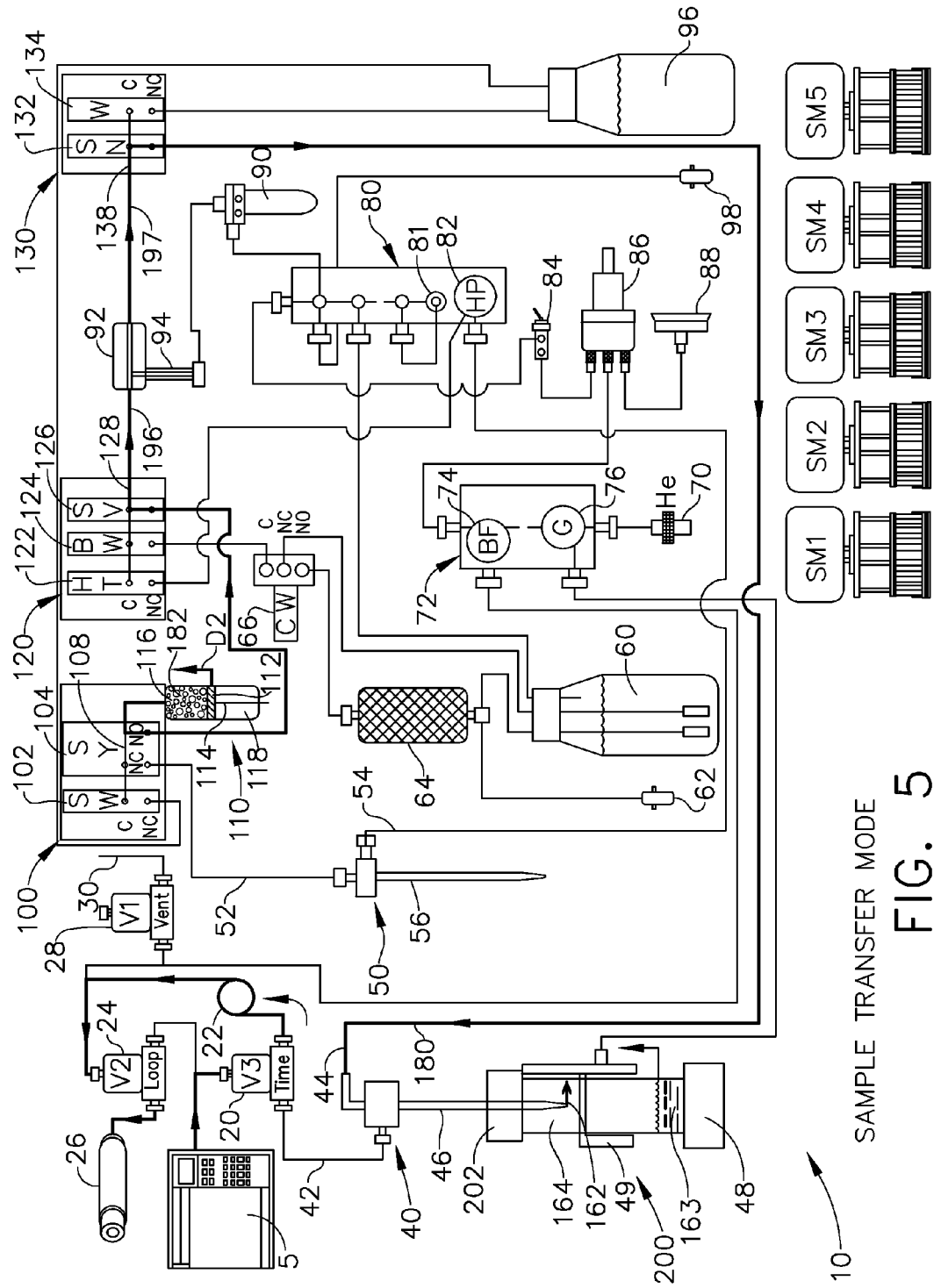
FIG. 5 SAMPLE TRANSFER MODE

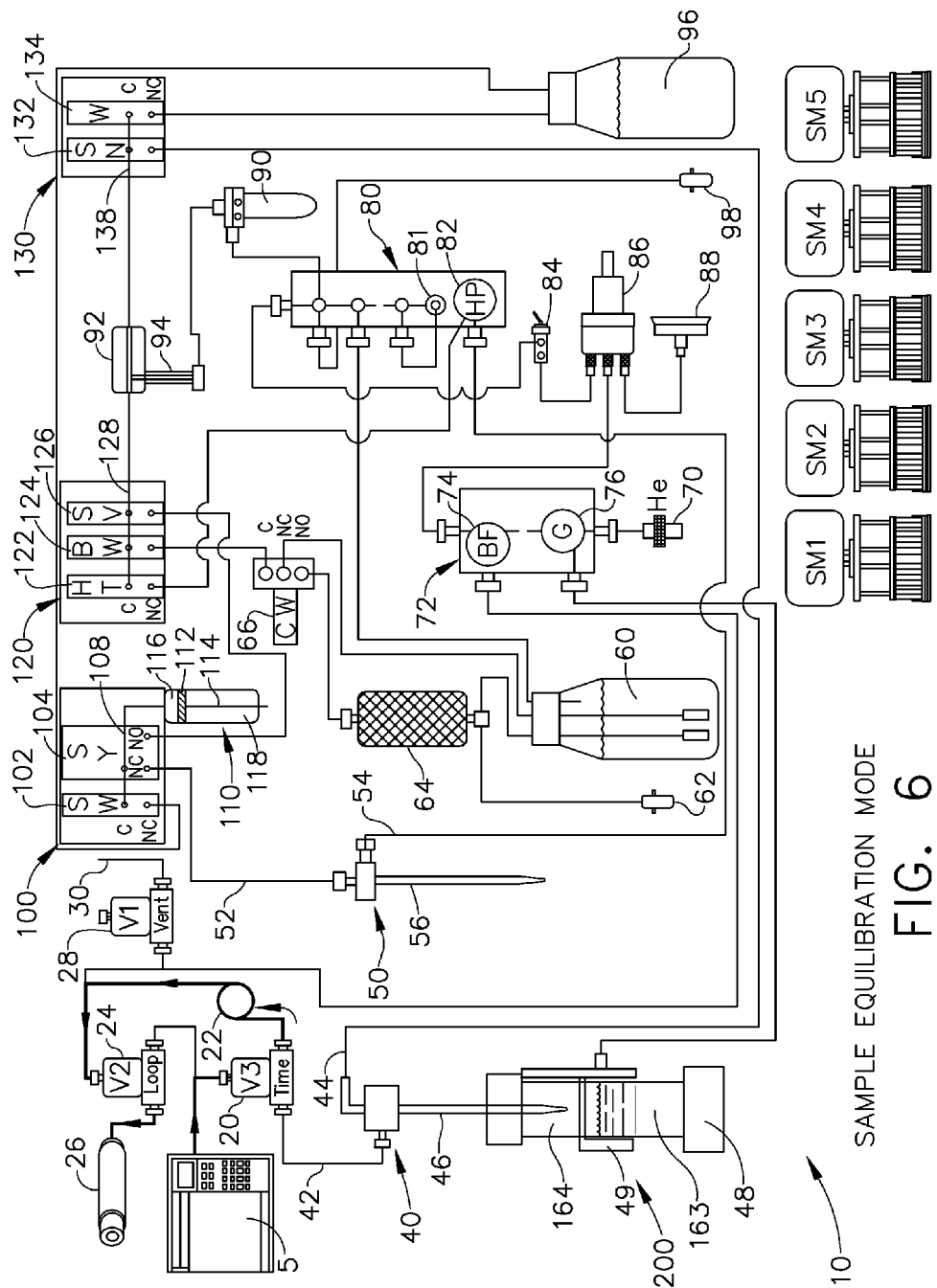
FIG. 6 SAMPLE EQUILIBRATION MODE

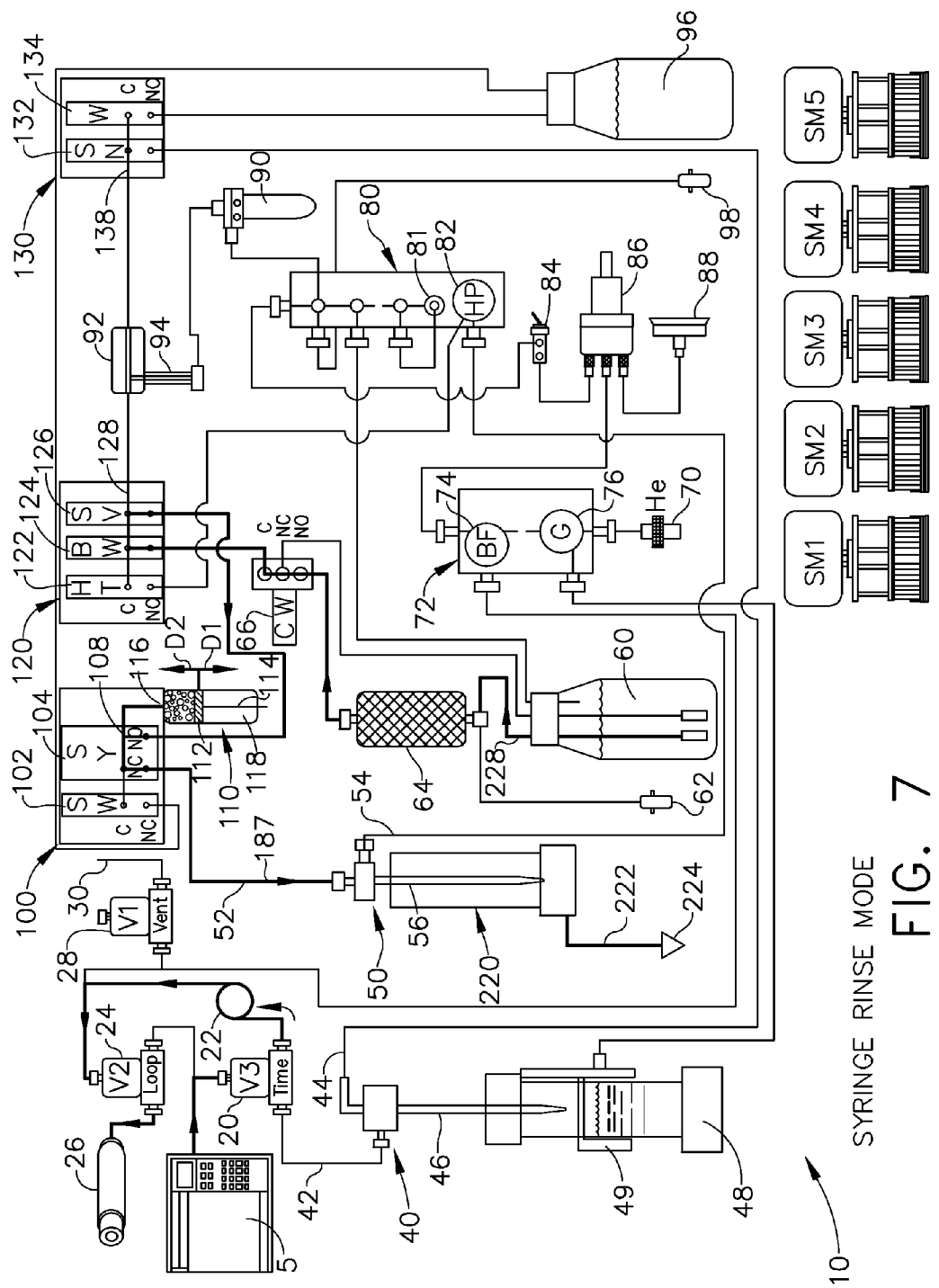
FIG. 7 SYRINGE RINSE MODE

NEEDLE RINSE MODE

FIG. 9 VIAL PRESSURIZATION MODE

VIAL EQUILIBRATION MODE

LOOP FILL MODE

FIG. 12 LOOP INJECT MODE

FIG. 13 TIME INJECT MODE

AUTOMATED SAMPLING OF DISSOLVED CONTAMINANTS IN WATER

TECHNICAL FIELD

The technology disclosed herein relates generally to chemical sampling equipment and is particularly directed to an automated sampler of the type which is capable of acquiring samples of contaminants that are dissolved in water. Embodiments are specifically disclosed as an automated sampler that places an initially empty, sealed first vial at a first sampling station, which has a dual-port concentric needle with flow passages for liquids and gasses to travel into and from the first vial. A mechanical syringe pump is provided to displace a programmable volume of gas from the first vial.

A sealed second vial that contains a field sample of water with dissolved contaminants is placed at a second sampling station, which also has a dual-port concentric needle with flow passages for liquids and gasses to travel into and from the second vial. The syringe pump extracts a programmed aqueous volume from the second vial into the enclosed displacement volume of the syringe. The syringe pump then transfers the programmed aqueous volume from the syringe's displacement volume into the first vial. In general, the programmed volume of field sample liquid is substantially equal to the volume of the gas that was earlier displaced from the first vial; after the aqueous field sample is transferred into the first vial, that vial now contains the same volume (and, therefore, exhibits the same pressure) as it had at the beginning of the procedure. All this is accomplished without exposing the field sample to any external gasses or other compounds, and without exposing the field sample to atmosphere, because the sealed vials are never opened during the sampling routine.

As part of the sample transfer routine, a spiked internal standard can optionally be added to the sample as it passes through the pathway to the first vial. This also is done without exposing the field sample to any external gasses or other compounds, and without opening the seal of the field sample to atmosphere.

The first sampling station houses a heated zone and a magnetic mixing mechanism. The field sample now in the first vial (typically in a liquid state when first transferred into the first vial) is heated to a programmable temperature setting along with an optional mixing of the sample. The sample can be heated for a programmed amount of time, or to a programmed temperature. An aliquot of headspace from the first vial is then injected into a Gas Chromatography device for identification and quantification.

STATEMENT REGARDING FEDERALLY SPONSORED RESEARCH OR DEVELOPMENT

None.

BACKGROUND

With the increased efforts for the United States to become more energy independent, tapping the natural gas reservoirs throughout the United States has long been a viable solution. However, until recently getting to many of these reserves has been very difficult. Now through the development of horizontal drilling combined with hydraulic fracturing, sometime called "hydrofracking," these reservoirs have become accessible. The drilling and fracturing techniques also raises Environmental concerns.

There is a need to develop and automate a sampling technique to address these energy and environmental concerns.

The EPA has developed a sampling test method, called RSK-175, which outlines the testing procedure for Dissolved Gasses, practically for types of natural gas, including methane, ethylene, and ethane (as well as others). This EPA test method involves some manual preparation of the water samples. The manual preparation can be time consuming, along with problems in maintaining sample integrity; the person working with the field sample must open the sample vial to take measurements. This causes two sample integrity problems: (1) the contents of the opened sample vial are exposed to the atmosphere of the testing lab; and (2) the dissolved gasses in the water of the field sample can quickly escape into the testing lab, thereby significantly degrading the quality of the measurements of that sample.

More specifically, the field sample vials are full of liquid and have no headspace, and since there is a need to create a headspace for a dissolved gas analysis, the operator will open the sealed vial and pour off a volume of the liquid sample to create some headspace in the vial. Unfortunately, this exposes the headspace to atmospheric air and can contaminate the sample, or it can cause the compound of interest to be lost during that manual sample preparation.

A second manual way for sampling or analyzing dissolved gasses is to pour some of the liquid sample into a smaller headspace vial (such as a 22 ml vial), and then cap it and seal it, again with zero headspace. The user will then use a manual syringe to pierce the seal with two separate needles. In a dual piercing step, 5 ml of air or some inert gas is injected through a first needle into the vial, to force 5 ml of the sample out of the vial through a second needle. This will create a 5 ml headspace. This vial then will end up with two punctures of the seal, or a much larger single puncture if the needle was a dual-port concentric needle. Later, during equilibration, there could be some leakage because of the earlier punctures in the seal. Even later, during the sample inject step, the vial seal must be punctured yet again, with possible further leakage.

Another type of field sample vial can be full of liquid (again without a headspace) that need to be sampled and analyzed, in which the compounds of interest are in a liquid state at the outset. Such liquid compounds could be in a //mixture with water, or other naturally-occurring chemicals, or perhaps mixed with other man-made compounds. Using conventional techniques, a person would open the sealed vial and pour out some of the contents into a second vial, and leave a headspace portion in that second vial, for later partitioning and sampling. Unfortunately, this again exposes the sample to possible contamination, and further, some of the compounds of interest could be lost by "boiling" into a vapor phase, and escaping the vial altogether, before the second vial is sealed. This is likely when working with "lighter" volatile organic compounds (VOCs), i.e., VOCs having a fairly low boiling point at atmospheric pressure.

Therefore, a need for an automated process is warrant, especially one that maintains sample integrity for the dissolved gasses or other contaminants.

SUMMARY

Accordingly, it is an advantage to provide an automated headspace sampler for use with water samples that contain dissolved contaminants, in which the system maintains sample integrity for the dissolved contaminants.

It is another advantage to provide an automated headspace sampler that provides sample integrity by not opening or piercing the sample vial in advance of the actual sampling, by providing a closed system that never exposes the sample to atmosphere.

It is yet another advantage to provide an automated headspace sampler that can be used with water samples that contain dissolved contaminants, and can also provide an automatic injection of an internal standard as part of the sample analysis routine.

It is still another advantage to provide an automated headspace sampler in which the field sample vial is pierced only once, and the piercing needle stays in the seal until after the compound of interest has been injected into the analyzing instrument.

It is a further advantage to provide an automated headspace sampler that uses a sealed field sample vial, an automatically-controlled syringe, and a headspace sample vial in conjunction with one another so that the dissolved contaminants in the liquid sample of the field sample vial are passed through the syringe and into the headspace sample vial, where they can be equilibrated into the headspace, and later injected into an analyzing instrument.

Additional advantages and other novel features will be set forth in part in the description that follows and in part will become apparent to those skilled in the art upon examination of the following or may be learned with the practice of the technology disclosed herein.

To achieve the foregoing and other advantages, and in accordance with one aspect, a method for sampling dissolved contaminants in liquid is provided, in which the method comprises the following steps: (a) providing a sampling system, having: (i) a first vial having a first seal, the first vial containing a first gas; (ii) a first needle subassembly having a first port and a second port proximal to a distal tip; (iii) a second vial having a second seal, the second vial being substantially filled with a liquid sample that contains dissolved contaminants; (iv) a second needle subassembly having a third port and a fourth port proximal to a distal tip; (v) a syringe having a movable plunger, the syringe having a displacement volume that is bounded by the movable plunger and by an outer wall of the syringe; (vi) a source of gas pressure; (vii) a waste outlet; (viii) a sample outlet; (ix) a plurality of fluidic passageways between the first port of the first needle subassembly, the second port of the first needle subassembly, the third port of the second needle subassembly, the fourth port of the second needle subassembly, the source of gas pressure, the displacement volume of the syringe, the sample outlet, and the waste outlet; (x) a plurality of automatically controlled valves that are in communication with the plurality of fluidic passageways and which, for a predetermined operating mode, establish at least one fluidic pathway of the plurality of fluidic passageways; and (xi) a system controller that determines one of the predetermined operating modes for controlling the plurality of automatically controlled valves; (b) using the first needle subassembly, piercing the first seal of the first vial; (c) using the movable plunger of the syringe, drawing a predetermined first volume of the first gas from the first vial, and evacuating the first volume of the first gas to the waste outlet, thereby establishing a partial vacuum condition inside the first vial; (d) using the second needle subassembly, piercing the second seal of the second vial; (e) using the movable plunger of the syringe, drawing a predetermined second volume of the liquid sample with dissolved contaminants from the second vial, and transferring the second volume of the liquid sample with dissolved contaminants into the first vial, wherein the first volume is substantially equal to the second volume, so that contents of the first vial now are not substantially under pressure or under vacuum conditions; (f) partitioning the liquid sample with dissolved contaminants into a headspace region of the first vial, thereby allowing at least a portion of the dissolved contaminants to enter the headspace region as headspace region vapor; and (g) transferring an aliquot of the headspace region vapor to the sample outlet.

In accordance with another aspect, a method for sampling liquids is provided, in which the method comprises the following steps: (a) providing a sampling system, having: (i) a first vial having a first seal, the first vial containing a first gas; (ii) a first needle subassembly having a first port and a second port proximal to a distal tip; (iii) a second vial having a second seal, the second vial being substantially filled with a liquid sample; (iv) a second needle subassembly having a third port and a fourth port proximal to a distal tip; (v) a syringe having a movable plunger, the syringe having a displacement volume that is bounded by the movable plunger and by an outer wall of the syringe; (vi) a source of gas pressure; (vii) a waste outlet; (viii) a sample outlet; (ix) a plurality of fluidic passageways between the first port of the first needle subassembly, the second port of the first needle subassembly, the third port of the second needle subassembly, the fourth port of the second needle subassembly, the source of gas pressure, the displacement volume of the syringe, the sample outlet, and the waste outlet; (x) a plurality of automatically controlled valves that are in communication with the plurality of fluidic passageways and which, for a predetermined operating mode, establish at least one fluidic pathway of the plurality of fluidic passageways; and (xi) a system controller that determines one of the predetermined operating modes for controlling the plurality of automatically controlled valves; (b) placing the first vial in a first position at the sampling system; (c) using the first needle subassembly, piercing the first seal of the first vial; (d) maintaining a sample integrity at the first seal by holding both the first needle subassembly and the first vial in their relative positions until after step (m) is completed; (e) using the movable plunger of the syringe, drawing a first volume of the first gas from the first vial, thereby establishing a partial vacuum condition inside the first vial; (f) using the movable plunger of the syringe, evacuating the first volume of the first gas to the waste outlet; (g) placing the second vial in a second position at the sampling system; (h) using the second needle subassembly, piercing the second seal of the second vial; (i) maintaining a sample integrity at the second seal by holding both the second needle subassembly and the second vial in their relative positions until after step (j) is completed; (j) using the movable plunger of the syringe, drawing a second volume of the liquid sample from the second vial; (k) using the movable plunger of the syringe, transferring the second volume of the liquid sample into the first vial; (l) partitioning the liquid sample into a headspace region of the first vial, thereby allowing at least a portion of the liquid sample to enter the headspace region as headspace region vapor; and (m) transferring an aliquot of the headspace region vapor to the sample outlet.

In accordance with yet another aspect, a method for sampling dissolved contaminants in liquid is provided, in which the method comprises the following steps: (a) providing a sampling system, having: (i) a first vial having a first seal, the first vial containing a first gas; (ii) a first needle subassembly having a first port and a second port proximal to a distal tip; (iii) a second vial having a second seal, the second vial being substantially filled with a liquid sample that contains dissolved contaminants; (iv) a second needle subassembly having a third port and a fourth port proximal to a distal tip; (v) a syringe having a movable plunger, the syringe having a displacement volume that is bounded by the movable plunger and by an outer wall of the syringe; (vi) a source of gas pressure; (vii) a waste outlet; (viii) a sample outlet; (ix) a container that holds an internal standard compound; (x) a plurality of fluidic passageways between the first port of the first needle subassembly, the second port of the first needle subassembly, the third port of the second needle subassembly, the fourth port of the second needle subassembly, the source of gas pressure, the displacement volume of the syringe, the sample outlet, the waste outlet, and the container holding an internal standard compound; (xi) a plurality of automatically controlled valves that are in communication with the plurality of fluidic passageways and which, for a predetermined operating mode, establish at least one fluidic pathway of the plurality of fluidic passageways; and (xii) a system controller that determines one of the predetermined operating modes for controlling the plurality of automatically controlled valves; (b) using the first needle subassembly, piercing the first seal of the first vial; (c) using the movable plunger of the syringe, drawing a first volume of the first gas from the first vial, thereby establishing a partial vacuum condition inside the first vial; (d) using the movable plunger of the syringe, evacuating the first volume of the first gas to the waste outlet; (e) using the second needle subassembly, piercing the second seal of the second vial; (f) using the movable plunger of the syringe, drawing a second volume of the liquid sample with dissolved contaminants from the second vial and into the displacement volume of the syringe; (g) using one of the plurality of automatically controlled valves, injected a third volume of the internal standard compound from the container into at least one of the plurality of fluidic passageways; (h) using the movable plunger of the syringe, transferring the second volume of the liquid sample with dissolved contaminants, along with the third volume of the internal standard compound, into the first vial; (i) partitioning the liquid sample with dissolved contaminants, and the internal standard compound, into a headspace region of the first vial, thereby allowing at least a portion of the dissolved contaminants and the internal standard compound to enter the headspace region as headspace region vapor; and (j) transferring an aliquot of the headspace region vapor and the internal standard compound to the sample outlet.

Still other advantages will become apparent to those skilled in this art from the following description and drawings wherein there is described and shown a preferred embodiment in one of the best modes contemplated for carrying out the technology. As will be realized, the technology disclosed herein is capable of other different embodiments, and its several details are capable of modification in various, obvious aspects all without departing from its principles. Accordingly, the drawings and descriptions will be regarded as illustrative in nature and not as restrictive.

BRIEF DESCRIPTION OF THE DRAWINGS

The accompanying drawings incorporated in and forming a part of the specification illustrate several aspects of the technology disclosed herein, and together with the description and claims serve to explain the principles of the technology. In the drawings:

FIG. 3B is a fluidic schematic diagram of the automated headspace sampler system of FIG. 1, showing the system in an operating mode called "Evacuation—Stage 1."

FIG. 3C is a fluidic schematic diagram of the automated headspace sampler system of FIG. 1, showing the system in an operating mode called "Evacuation—Stage 2."

FIG. 3D is a fluidic schematic diagram of the automated headspace sampler system of FIG. 1, showing the system in an operating mode called "Evacuation—Stage 3."

FIG. 4B is a fluidic schematic diagram of the automated headspace sampler system of FIG. 1, showing the system in an operating mode called "Inject Internal Standard."

FIG. 5 is a fluidic schematic diagram of the automated headspace sampler system of FIG. 1, showing the system in an operating mode called "Sample Transfer."

FIG. 6 is a fluidic schematic diagram of the automated headspace sampler system of FIG. 1, showing the system in an operating mode called "Sample Equilibration."

FIG. 7 is a fluidic schematic diagram of the automated headspace sampler system of FIG. 1, showing the system in an operating mode called "Syringe Rinse."

DETAILED DESCRIPTION

Figure 1:
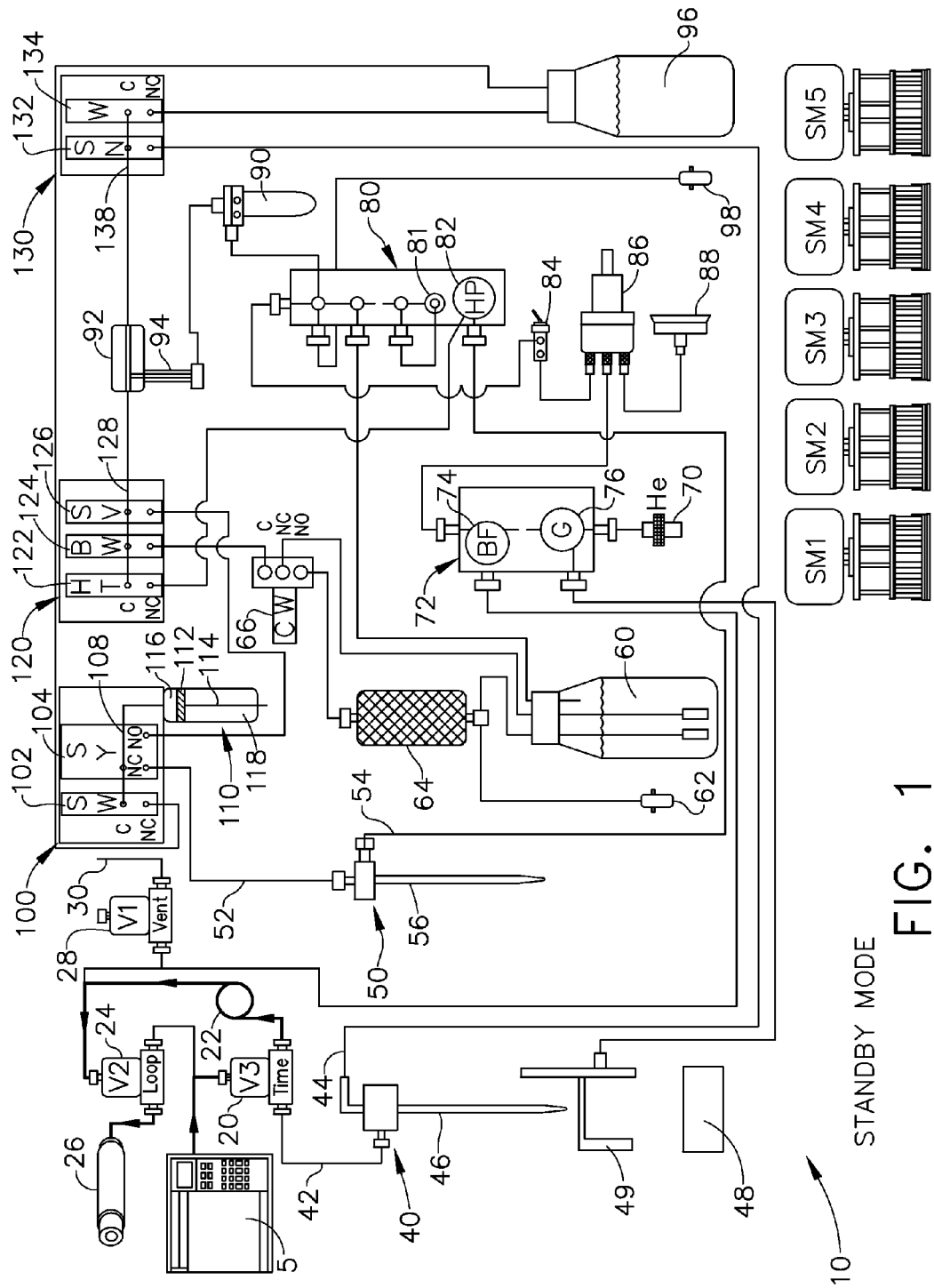
FIG. 1 is a fluidic schematic diagram of a automated headspace sampler system constructed according to the principles of the technology disclosed herein, showing the system in an operating mode called "Standby."

Reference will now be made in detail to the present preferred embodiment, an example of which is illustrated in the accompanying drawings, wherein like numerals indicate the same elements throughout the views.

It is to be understood that the technology disclosed herein is not limited in its application to the details of construction and the arrangement of components set forth in the following description or illustrated in the drawings. The technology disclosed herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings.

The terms "first" and "second" preceding an element name, e.g., first inlet, second inlet, etc., are used for identification purposes to distinguish between similar or related elements, results or concepts, and are not intended to necessarily imply order, nor are the terms "first" and "second" intended to preclude the inclusion of additional similar or related elements, results or concepts, unless otherwise indicated.

In addition, it should be understood that embodiments disclosed herein include both hardware and electronic components or modules that, for purposes of discussion, may be illustrated and described as if the majority of the components were implemented solely in hardware.

However, one of ordinary skill in the art, and based on a reading of this detailed description, would recognize that, in at least one embodiment, the electronic based aspects of the technology disclosed herein may be implemented in software. As such, it should be noted that a plurality of hardware and software-based devices, as well as a plurality of different structural components may be utilized to implement the technology disclosed herein.

It will be understood that the term "circuit" as used herein can represent an actual electronic circuit, such as an integrated circuit chip (or a portion thereof), or it can represent a function that is performed by a processing device, such as a microprocessor or an ASIC that includes a logic state machine or another form of processing element (including a sequential processing device). A specific type of circuit could be an analog circuit or a digital circuit of some type, although such a circuit possibly could be implemented in software by a logic state machine or a sequential processor. In other words, if a processing circuit is used to perform a desired function used in the technology disclosed herein (such as a demodulation function), then there might not be a specific "circuit" that could be called a "demodulation circuit;" however, there would be a demodulation "function" that is performed by the software. In addition to the above, the term "circuit" can represent one or more fluidic pathways or passageways (for either gasses or liquids), with control valves or solenoids that are automatically controlled to alter the direction of those pathways, as desired. All of these possibilities are contemplated by the inventors, and are within the principles of the technology when discussing a "circuit."

An overview of the technology disclosed herein is now provided: an auto sampler with a gripper device to pick and place a first, initially empty, sealed vial in a sampling station (the "first station"). The first station includes a heated sampling cup, a mixing mechanism, and a dual-port concentric "headspace needle" with flow passages for liquids and gasses to travel into and from the first vial. A mechanical syringe pump is provided to displace a programmable volume of air (or inert gas) from the first (sealed) vial. The syringe pump then extracts a programmed aqueous volume from a second vial at a second sampling station (the "second station"), which includes a dual-port concentric "sample needle" with flow passages for liquid and gas to travel into and from the second vial. The second vial contains a field sample; typically this field sample comprises dissolved gasses (or other contaminants) in water. The second vial is normally sealed, and is (substantially) completely filled with the water (field) sample. The syringe pump then transfers the programmed aqueous volume from the second vial to the first vial, via the syringe. As part of the sample transfer routine, a spiked internal standard is optionally added to the sample as it passes through the pathway to the first vial.

The first station houses a heated zone and a magnetic mixing mechanism. The sample in the first vial (typically in a liquid state when first transferred into the first vial) is heated to a programmable temperature setting along with an optional mixing (i.e., stirring) of the sample. The sample can be heated for a programmed amount of time, or to a programmed temperature. An aliquot of headspace from the first vial is then injected into a Gas Chromatography device for identification and quantification.

Referring now to FIG. 1, a fluidic schematic diagram is provided for a "Standby" Mode, in which the system is essentially quiescent, and the only fluidic flow is sourced from a GC instrument 5 through solenoid valves V3 and V2, and to a heater element 26 that leads back to the input of the GC device. The exit side of heater element 26 is at a "sample outlet" of the system 10, via a fluidic passageway between the heater element 26 and the physical input of the GC device 5.

Several different fluidic diagrams are provided herewith, and they all generally contain the same hardware, but are configured in different arrangements. This description will start by introducing the hardware.

The GC device is a gas chromatography instrument, designated by the reference numeral 5, and there are fluidic pathways that lead to a solenoid valve 20, also known as V3, and to a second solenoid valve 24, also known as V2. The output of solenoid valve V2 leads to a heater 26, and any gasses leading to the heater 26 will then presented back to the input of the GC device 5.

The solenoid valve V3 also has a port that leads to a fixed volume sample loop 22, which then leads back to the solenoid valve V2. There also is a solenoid valve 28, known as V1. Gasses leading to its input port can be exhausted to a vent through a pathway 30.

In this Standby Mode of FIG. 1, all of the solenoid valves are de-energized, or "off," and the pathways that are normally open allow helium gas to flow from the GC device 5 through the valve V3, through the sample loop 22, through the valve V2, and back to the heater 26. These three solenoid valves also have normally closed passageways that will be used in other operating modes.

In FIG. 1, the overall device or system is generally designated by the reference numeral 10, which includes two sampling stations, and many other solenoid valves and fluidic pathways. It also includes five stepper motors, and a system controller that is not shown on FIG. 1. The two sampling stations will generally be referred to herein as the "first station" and the "second station." Both of these stations have sampling needles that can be inserted into sealed vials that can contain a liquid or gaseous sample, or that can be initially empty, but can receive liquid or gaseous compounds into the vial itself, and later have its headspace sampled (or swept). There also is a syringe with a moveable plunger that is controlled by the system controller.

The first station is generally designated by the reference numeral 40, and contains a dual-port concentric needle 46; needle 46 is also sometimes referred to herein as a needle subassembly. The two openings in the needle are proximal to the bottom (or tip) of that needle (not directly visible on FIG.

1) and they are fluidically connected to external fluidic pathways 42 and 44. The first station includes a vial gripper 49, and an elevator 48. The overall gas extractor system 10 includes a tray that holds multiple sample vials, and the gripper 49 can be controlled in three axes by the various stepper motors.

The stepper motors on FIG. 1 are designated SM1, SM2, SM3, SM4, and SM5. SM1 controls the position of a plunger 114 for a syringe subassembly 110. SM2 controls the Z-axis movements of the gripper 49. SM 3 controls the Z-axis position of the sample needle 56. Stepper motors SM4 and SM5 control the X-axis and Y-axis movements of the gripper 49, respectively.

The second station is generally designated by the reference numeral 50, which also includes a dual-port concentric needle 56; needle 56 is also sometimes referred to herein as a needle subassembly. There are two small openings proximal to the bottom (or tip) of the needle 56 that are not directly visible on FIG. 1. Those openings are in fluidic communication with two external fluidic pathways 52 and 54. The needle 56 will sometimes be referred to herein as the "sample needle;" the needle 46 will sometimes be referred to herein as the "headspace needle." For needles 46 and 56, the needle ports (or openings) are typically positioned so that one opening is located right at the narrowed tip, and the other opening is located fairly close to the tip, but somewhat up from the tip, along one side of the needle's shaft. Various other needle subassembly port positioning arrangements could be used, or alternatively two separate single needles could be used as a needle subassembly (perhaps with somewhat less beneficial results).

A rinse water reservoir is included at reference numeral 60, and it has an associated overflow vent at 62, which includes a 25 PSI check valve. One pathway leaving the rinse water reservoir travels through a water heater 64, and that pathway leads to a solenoid valve 66, also designated "CW" for cold water.

A helium manifold is provided, and is generally designated by the reference numeral 72. There is a helium gas input at 70, which is connected to a helium source at about 60-80 PSI (not shown on FIG. 1). Attached to the helium manifold 72 is a backflush valve 74, which is also designated "BF," and also there is a gripper solenoid 76 that is also designated "G." The helium gas can travel through a pathway internal to the helium manifold as shown on the drawing. It will be understood that helium is not the only type of inert gas that can be used in the system 10. Other elements or compounds may be used instead of helium in many applications, including gasses such as nitrogen ($N_2$), or other inert gasses, including argon, neon, etc.

The helium gas can be directed to a pressure regulator at 86, which is used to output a regulated pressure at about 15 PSI (above atmosphere). A pressure gauge 88 is provided so that the user can monitor this regulated pressure. The regulated pressure travels through a pathway to a toggle switch 84, which is manual control operated by the user to allow the helium gas to be sent to the rest of the system 10, or to be turned off at a time when system 10 is not being used at all. The helium gas then travels to another manifold, generally designated by the reference numeral 80.

Reference numeral 80 is another multi-port manifold, and it includes a flow restrictor 81 that restricts the flow therethrough to about 200 milliliters per minute, at the 15 PSI helium feed pressure coming from the pressure regulator 86. This manifold 80 also includes a solenoid valve 82 that is designated HP (for helium pathway), and this HP solenoid can direct the helium toward two different passageways (pathways).

A holding tank at the reference numeral 90 is provided to hold an internal standard fluid; also this is referred to as the I.S. holding tank. There is an internal standard manifold 92 which contains a small injector 94 that will be described below. There is another overflow vent at 98, that connects into the manifold 80.

The system 10 is provided with a syringe pumping manifold, generally designated by the reference numeral 100. Mounted to this manifold 100 is a solenoid valve 102 that is also referred to the "SW" solenoid (for syringe waste). Also mounted to the manifold 100 is a solenoid valve 104 that is referred to as "SY" (for syringe solenoid). There is a internal pathway 108 that runs through the manifold 100 which is connected to the common port of the solenoids SW and SY, and also is fluidically connected to an upper displacement volume 116 of a syringe subassembly 110. The syringe 110 contains a plunger 112, a drive rod 114, and an outer syringe barrel, and the barrel contains two displacement volumes 116 and 118. The lower displacement volume 118 is open to atmosphere, while the upper displacement volume 116 is in fluidic communication with the internal common pathway 108 of the manifold 100.

System 10 includes a three-input mixing manifold, generally designated by the reference numeral 120. Manifold 120 has three solenoid valves attached thereto, including a valve 122 also known as the "HT" valve (for helium transfer), a valve 124 also known as the "BW" valve (for blank water), and finally a valve 126 also known as the "SV" valve (for sample valve). There is a common internal pathway 128 that is connected to the common input port of all three solenoids 122, 124, and 126.

System 10 includes a transfer manifold, generally designated by the reference numeral 130. This transfer manifold 130 has two solenoid valves mounted thereto, including a solenoid valve 132 also known as the "SN" solenoid (for soil needle), and a solenoid valve 134 also known as the "W" solenoid (for waste). There is a common pathway 138 through the transfer manifold 130 that connects to the common input port of both of the solenoid valves 132 and 134. The normally closed port of the solenoid W is connected (via a passageway) to a waste holding container 96. Also, the normally closed port of the SW solenoid (on the manifold 100) also is connected (via a passageway) to the waste holding container 96. These are waste outlets.

The above description of the system hardware will now be used to describe the various stages or steps of the methodology used in the technology disclosed herein. There are multiple stages, which will generally be referred to herein as "modes" of operation, and the various control valves or solenoids are controlled by the system controller 250, as needed. A control logic table is presented below to succinctly show the operating status of each of the control valves and solenoids during these operating modes. A more detailed description of these modes of operation will follow. In TABLE 1, a logic "0" means OFF or "de-energized," while a logic "1" means ON or "energized;" also, a logic "C" means the device cycles both on and off at controlled time intervals during the step.

TABLE 1

| Step # | V1 | V2 | V3 | SW | SY | HT | BW | SV | SN | W | CW | BF | G | HP | IS | Plunger |
|---|---|---|---|---|---|---|---|---|---|---|---|---|---|---|---|---|
| 1 | 0 | 0 | 0 | 0 | 0 | 0 | 0 | 0 | 0 | 0 | 0 | 0 | 0 | 0 | 0 | up |
| 2 | 0 | 1 | 1 | 0 | 0 | 1 | 0 | 0 | 1 | 0 | 0 | 1 | 0 | 0 | 0 | up |
| 3A | 1 | 1 | 1 | 0 | 0 | 1 | 0 | 0 | 1 | 0 | 0 | 0 | 0 | 0 | 0 | up |
| 3B | 1 | 1 | 1 | 0 | 0 | 1 | 0 | 0 | 0 | 1 | 0 | 0 | 0 | 0 | 0 | up |
| 3C | 0 | 0 | 0 | 0 | 0 | 0 | 0 | 1 | 1 | 0 | 0 | 0 | 0 | 0 | 0 | downward |
| 3D | 0 | 0 | 0 | 1 | 0 | 0 | 0 | 0 | 0 | 0 | 0 | 0 | 0 | 0 | 0 | upward |
| 4A | 0 | 0 | 0 | 0 | 1 | 0 | 0 | 0 | 0 | 0 | 0 | 0 | 0 | 1 | 0 | downward |
| 4B | 0 | 0 | 0 | 0 | 0 | 0 | 0 | 1 | 1 | 0 | 0 | 0 | 0 | 0 | 1 | down |
| 5 | 0 | 0 | 0 | 0 | 0 | 0 | 0 | 1 | 1 | 0 | 0 | 0 | 0 | 0 | 0 | upward |
| 6 | 0 | 0 | 0 | 0 | 0 | 0 | 0 | 0 | 0 | 0 | 0 | 0 | 0 | 0 | 0 | up |
| 7 | 0 | 0 | 0 | 0 | C | 0 | 1 | 1 | 0 | 0 | 0 | 0 | 0 | 0 | 0 | cycles |
| 8 | 0 | 0 | 0 | 0 | C | 1 | 0 | 1 | 0 | 0 | 0 | 0 | 0 | 0 | 0 | cycles |
| 9 | 0 | 0 | 0 | 0 | 0 | 1 | 0 | 0 | 1 | 0 | 0 | 0 | 0 | 0 | 0 | up |
| 10 | 0 | 0 | 0 | 0 | 0 | 0 | 0 | 0 | 0 | 0 | 0 | 0 | 0 | 0 | 0 | up |
| 11 | 1 | 1 | 1 | 0 | 0 | 0 | 0 | 0 | 0 | 0 | 0 | 0 | 0 | 0 | 0 | up |
| 12 | 0 | 0 | 0 | 0 | 0 | 0 | 0 | 0 | 0 | 0 | 0 | 0 | 0 | 0 | 0 | up |
| 13 | 0 | 0 | 1 | 0 | 0 | 0 | 0 | 0 | 0 | 0 | 0 | 0 | 0 | 0 | 0 | up |

Figure 2:
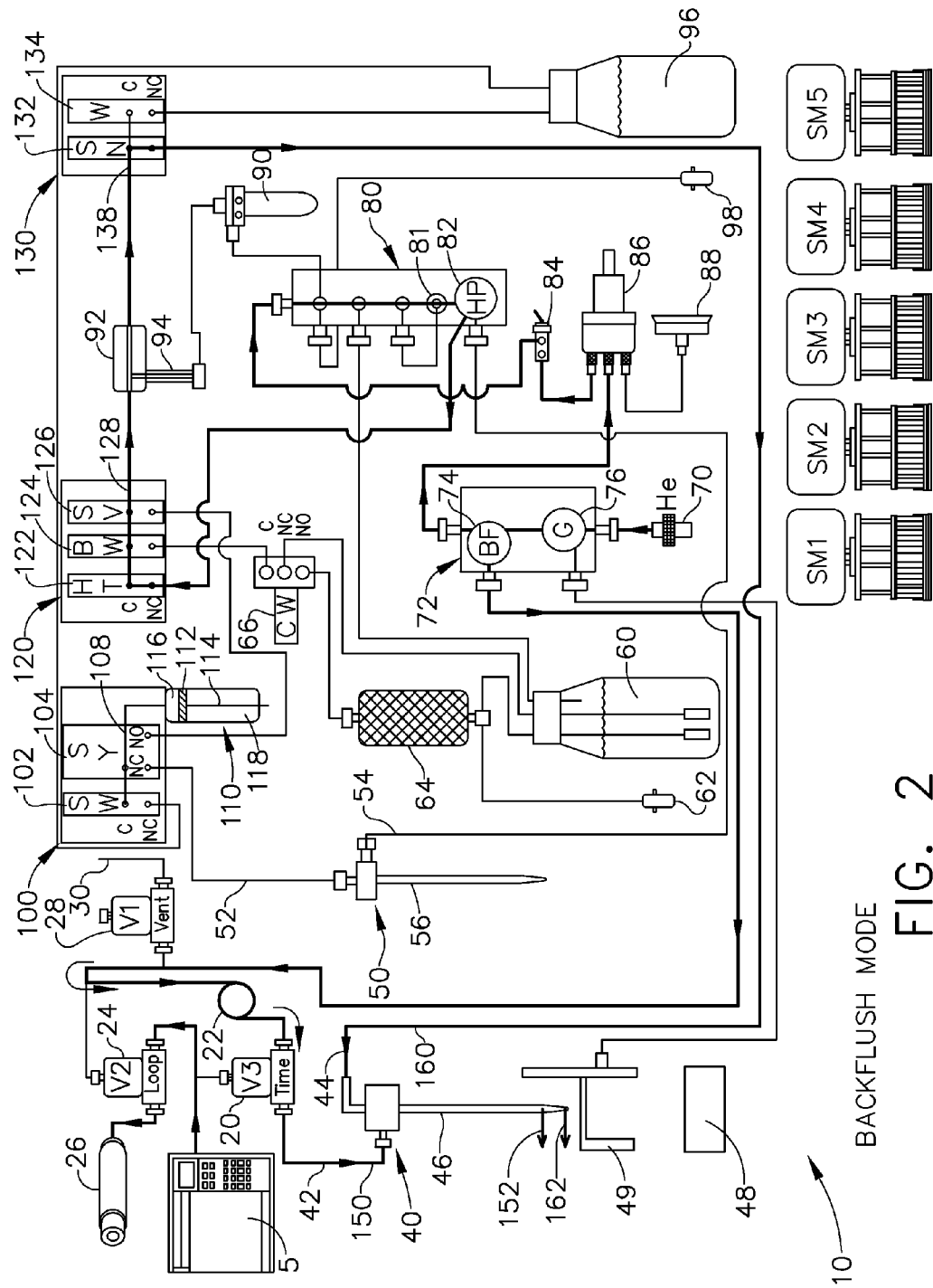
FIG. 2 is a fluidic schematic diagram of the automated headspace sampler system of FIG. 1, showing the system in an operating mode called "Backflush."

Referring now to FIG. 2, the system 10 is now shown in a configuration known as the Backflush Mode. In this mode, helium gas is input at 70, then travels through a pathway and through the BF solenoid in both directions, in which the first pathway goes through the sample loop 22 and the V3 solenoid and arrives at the headspace needle at the first station 40, via a pathway 150. This blows helium gas through the headspace needle 46 and out one of its ports near the bottom, through a pathway 152. This helium is exhausted to atmosphere. In the backflush mode, the solenoids V2 and V3 are both on, as well as the solenoids HT, SN, and BF.

The other helium pathway from the BF solenoid leads through the pressure regulator 86, through the manifold 80, through the HT solenoid and the SN solenoid, and arrives at a pathway 160 to the headspace needle 46. This helium gas is output at the very bottom of the headspace needle 46 through a pathway 162. This helium gas is then exhausted to atmosphere. In general, the Backflush Mode illustrated in FIG. 2 is merely flushing out the system before its next use.

Figure 3A:
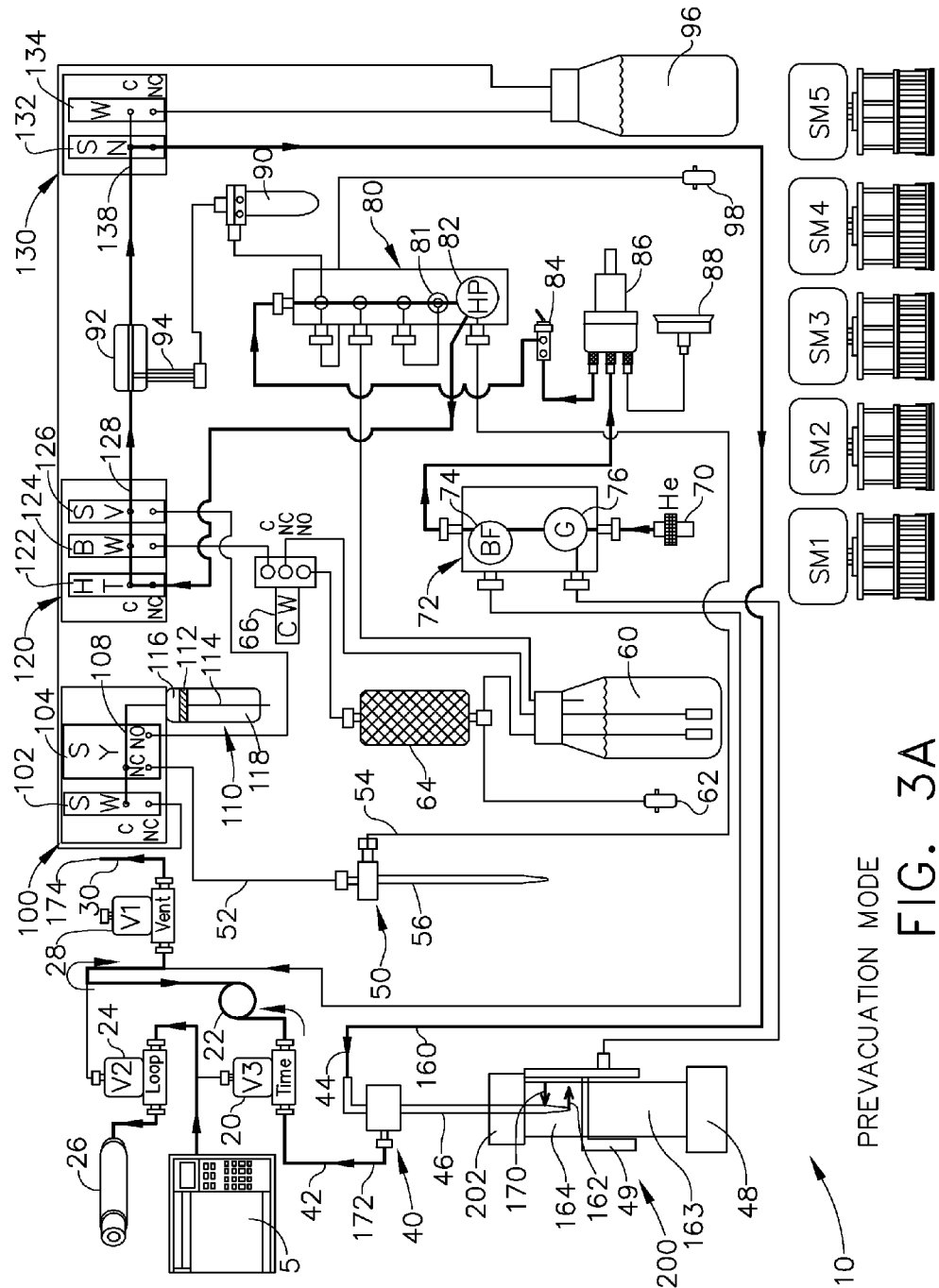
FIG. 3A is a fluidic schematic diagram of the automated headspace sampler system of FIG. 1, showing the system in an operating mode called "Prevacuation."

Referring now to FIG. 3A, which is referred to as the Prevacuation Mode. It will be understood that this Prevacuation Mode at FIG. 3A is only a first step in an overall "evacuation" operation that is illustrated in FIGS. 3A, 3B, 3C, and 3D. In general, these modes of evacuation are sweeping the "old air" from the empty vial that will be mounted at the first station, to eliminate any old sample or atmospheric air from that vial before it receives new sample gasses or liquids.

On FIG. 3A the first vial, generally designated by the reference numeral 200, is positioned at the first station on the elevator 48. This first vial was previously resting on a tray that contain many such vials, then selected by the controller, which commanded the gripper to move to the appropriate X and Y axes coordinates, and then the Z-axis stepper motor (SM2) moved to position the gripper appropriately to grab the correct empty vial from the tray. All three of the stepper motors were then used to move this empty vial to the first station, as illustrated in FIG. 3A.

The vial 200 has a seal and cap at 202, so that its contents will remain separated from atmospheric air, or from any of the gaseous components that are in the area of the automated sample system 10. At the start of the Prevacuation Mode, the solenoid BF is turned off, and the solenoid V1 (the "vent" solenoid) is turned on. Helium gas continues to run through the pathway 160 into the vial, and then exits the bottom of the headspace needle at the pathway 162. If the vial for some reason were contain some type of liquid, that liquid would be at the bottom portion of the vial at 163, and there would be a headspace volume at 164. In general, the vial 200 will be empty of liquid at this point in the sampling procedure.

The gas that exits the bottom port of the headspace needle at 162 will now cause a gas flow to reenter the other port of this dual-port needle, via the pathway 170, thereby sweeping the "old air" from the vial by this helium flow.

That swept gas will continue out the pathway 172, through the solenoid V3, through the sample loop 22, and through the vent valve V1, and out the vent via a flow 174. This Prevacuation Mode will continue for about 13 seconds, as determined by the controller, which is discussed below in the flow chart of FIGS. 15-19.

Referring now to FIG. 3B, the system 10 is now in an Evacuation Mode—Stage 1. The main difference between FIGS. 3A and 3B is that in the Prevacuation Mode of FIG. 3A, the SN solenoid was on, and in Evacuation Stage 1, solenoid SN is turned off and instead solenoid W is turned on. This directs the helium input gas from input 70 through the W solenoid and that directs the gas into the waste holding container 96. There is now no gas flow into the first vial at the first station, but there is still a gas flow that can escape the first vial through the pathway 170 from the headspace 164. This allows the contents of the vial to decant to the vent at 174. This also allows any excess pressure that was in the vial to be relieved through the vent 174. The Evacuation Stage 1 will last for a predetermined time, as determined by the system controller, which will last for approximately 5 seconds, as per the flow chart FIGS. 15-19.

Referring now to FIG. 3C, the system 10 is now in Evacuation Mode—Stage 2. In this mode, the solenoids SV and SN are turned on, and all other solenoids are turned off. The helium input gas at 70 has nowhere to go in this condition. The main action occurs at the syringe 110, in which the plunger 112 is pulled down by the stepper motor SM1 acting on the syringe rod 114. This pulls some more headspace gas from the vial 200 out of the headspace volume 164, and that gas is moved into the upper displacement volume of the syringe at 182. As seen FIG. 3C, the plunger 112 is pulled in the direction D1.

This action of the syringe has the effect of pulling a small vacuum on the headspace of the vial 200. But more specifically, a certain amount of gas volume is being removed from the vial 200, so it will later be able to receive the same volume of sample liquid (or gas) at a later stage in the operation of the equipment 10. The exact amount of volume of gas being removed from the vial and into the syringe is under the control of the system controller, which will determine how much time the stepper motor SM1 will be actuated to produce the correct amount of displacement volume 182 inside the syringe 110. As can be seen in FIG. 3C, the gas flow leaves the vial at the pathway 170 through the upper port of the headspace needle 46, and travels through a pathway 180 into the SN valve, through the internal standard manifold 92, through the SV valve, through the normally port of the SY valve, and into the syringe displacement volume 182.

Referring now to FIG. 3D, the system 10 is now in an Evacuation Mode—Stage 3. In this mode, the SW solenoid valve is turned on, and all other solenoid valves are turned off. Helium gas at the input 70 has nowhere to go in this mode. Stepper motor SM1 is operated to push the syringe plunger back upward (in this view), which is in the direction D2. This pushes the gasses 182 in the displacement volume 116 out of the plunger, through the SW solenoid, and down into the waste holding container 96, via the pathway 178. Whatever gasses are in the volume 182 of the syringe are now effectively disposed of. (In general, these should be helium or other inert gasses, if the vial 200 was empty at the beginning of the procedure.)

Figure 4A:
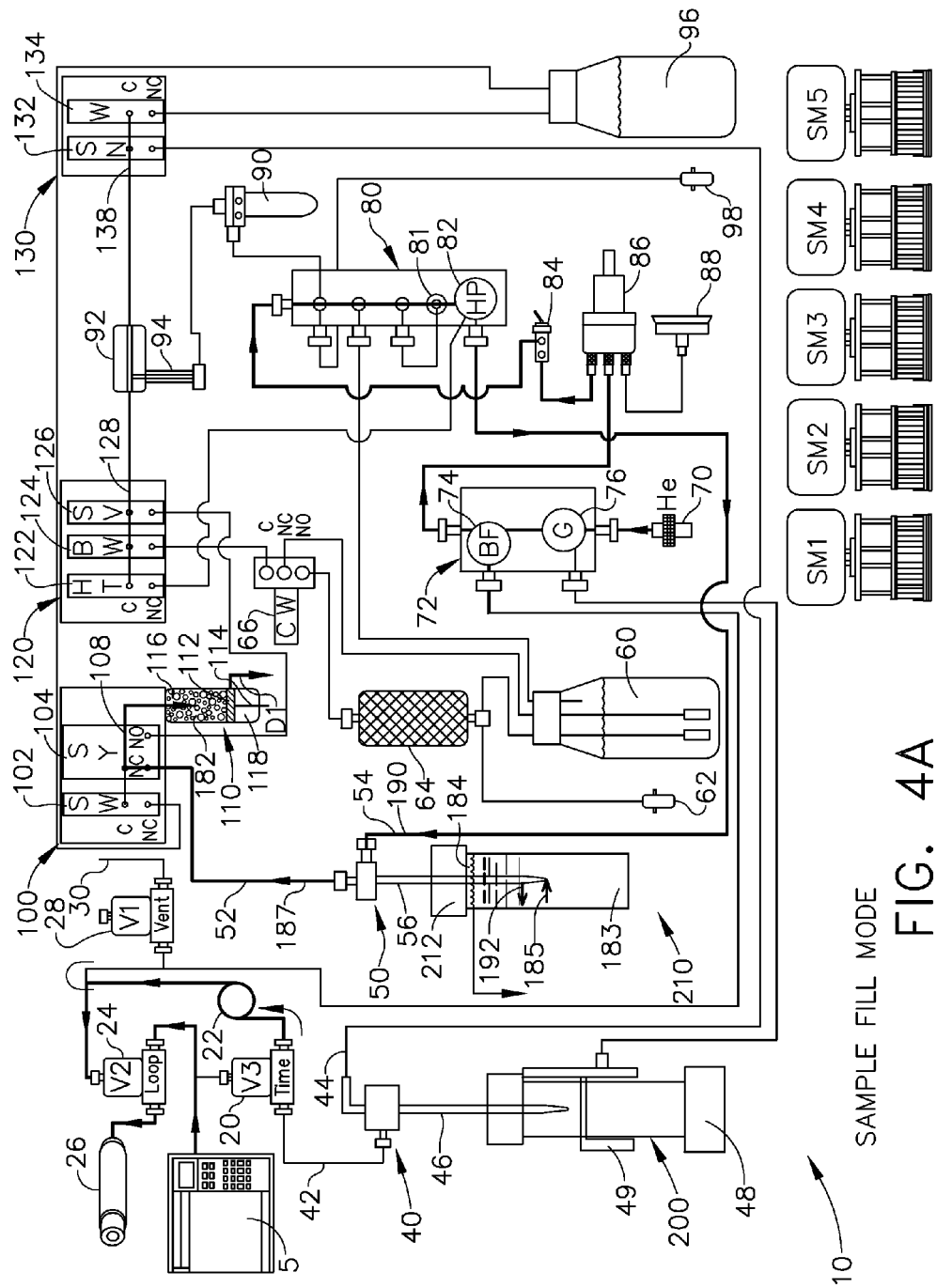
FIG. 4A is a fluidic schematic diagram of the automated headspace sampler system of FIG. 1, showing the system in an operating mode called "Sample Fill."

Referring now to FIG. 4A, the system 10 is now in a Sample Fill Mode, in which a second vial, generally designated by the reference numeral 210, is introduced into the system. The second vial is position on the second station 50, so that the sample needle 56 punctures the seal and cap 212 of the second vial 210. This second vial will normally contain a liquid field sample 183; there could be a small portion of the vial that has some headspace gasses at 184. For analyzing dissolved contaminants in water, however, the second vial 210 is typically filled with liquid, without any headspace. A portion of the liquid is going to be taken from the second vial by the sample needle 56 and placed into the syringe 110.

In this Sample Fill Mode, the solenoids SY and HP are turned on, and all other solenoids are off. The input helium gas at 70 is run through the helium manifold 72, and through the multi-port manifold 80, out through the HP valve and into the pathway 190, where this gas is introduced through the pathway 192 into the second vial. This pressurization of the vial (using the helium gas as the impetus) will cause some of the liquid sample to leave through the bottom port of the sample needle 56, through the pathway 185. This liquid will travel up the pathway 187, through the SY valve (through its normally closed port) and into the upper displacement volume of the syringe, as the plunger of the syringe is drawn in the direction D1. This will introduce sample liquid into the syringe at 182.

Referring now to FIG. 4B, the system 10 is now in an Inject Internal Standard Mode. In this mode of operation, the solenoids SV and SN are turned on, and all other solenoids are turned off. The plunger 112 of the syringe is at its down position, so that the sample that was taken in the previous step from the second vial will temporarily remain in the syringe, in the upper displacement volume 116. The sample is represented at the reference numeral 182. There is small solenoid 94 that is mounted to the internal standard manifold 92, and that solenoid will now inject (or "spike") a small amount of the internal standard fluid from the internal standard holding tank 193.

The internal standard holding tank 193 is pressurized by the helium gasses from the helium input source 70, through the helium manifold 92 and the multi-port manifold 80, as shown on FIG. 4B. When the system controller commands the small solenoid 94 to inject, a predetermined volume of internal standard fluid will move through the pathway 194, through the small injection nozzle pathway 195, and this spiked internal standard fluid will end up in the pathways 196 and 197. This internal standard fluid really cannot go any further than those two pathways 196 and 197 right at this time, because everything else in the system is deadheaded, and other fluids are not flowing anywhere else momentarily.

This internal standard injection is an optional step, and it may or may not be used by a specific user for a specific application. The actual composition of the internal standard can either be a liquid or a gas, as determined by the specific application. The specific amount will be predetermined by the user, and the system controller will instruct internal standard injector 94 exactly how much of the fluid is to be injected into the pathway 195. These trace amounts of the internal standard will later be measurable by the GC instrument, and can be used to help calibrate the overall measurements taken of the sample, as desired by the user.

Referring now to FIG. 5, the system 10 is now in a Sample Transfer Mode. In this mode of operation, the SV and SN solenoids are still left on, and the plunger of the syringe is now moved upward by the stepper motor SM1, so that the plunger moves in the direction D2. The sample 182 that is sitting in the syringe 110 is now pushed out and eventually ends up in the first vial 200. As the sample is being transferred, it leaves the SY solenoid and travels through the SV solenoid, the internal standard manifold, the SN solenoid, and finally arrives at the pathway 180 so that it is moved through the bottom port of the headspace needle 46, via the pathway 162, and into the first vial 200.

The Sample Transfer Mode is the final step of moving the compound that was taken from the second vial 210 through the sample needle 56, first into the syringe 110, and later exiting the syringe and now being moved to the first vial 200 through the headspace needle 46. Eventually some of this sample material will be directed to the input port of the GC device 5, and all of this will occur without the sample contaminants from the initial liquid sample ever having been exposed to atmosphere, thereby controlling their environment throughout the sample extraction procedure. This is a critical step in the process of obtaining accurate chemical sampling of the dissolved contaminants that were in the liquid sample of the second vial 210 as that field sample vial was first introduced into the system in the Sample Fill step, illustrated in FIG. 4A. This new procedure is a vast improvement over the EPA existing sampling procedures, and cannot be done by any manual technique known in the conventional art.

Referring now to FIG. 6, the system 10 has now entered a Sample Equilibration Mode. In this mode, all the solenoids are turned off and there are no gasses or samples being moved through the system, except for the small amount of helium gas running through the solenoids V2 and V3 from the GC device, and being looped back to the GC input. The sample that is in the first vial 200 is now equilibrating, and the compounds of interest that are in the liquid phase 163 are being partitioned into the gas phase in the headspace 164. If desired, the vial 200 can be heated and mixed, to increase the partitioning factor. These are control variables that the user can enter into the system controller, as desired.

Referring now to FIG. 7, the system 10 is now in a Syringe Rinse Mode. This occurs while the first vial 200 is equilibrating, which will take some time. Instead of wasting that time, this Syringe Rinse Mode will clean the sample needle 56. A wash station 220 is mounted on the sample needle 56, and this wash station has a drain line 222 that leads to a sink 224. The solenoids that are turned on during this step are the SY solenoid, and the BW and SV solenoids. Rinse water is taken from the reservoir 60 and runs through the pathway 228 through the CW solenoid and into the BW and SV solenoids. This rinse water is further directed into the syringe pumper manifold 100, where it is introduced into the upper displacement volume 116 of the syringe. The syringe plunger is now moved up and down cyclically, in both directions D1 and D2. The SY solenoid is cyclically turned on and off, depending on whether the rinse water is being introduced into the syringe, or being exiting from the syringe through a pathway 187 into the wash station 220. As the rinse water is being introduced into the syringe, the SY valve is left off so that the rinse water can flow through its normally open port. Then when the syringe is full, its plunger will be moved in the direction D2 as the SY valve is energized, and thereby allows the rinse water to exit the syringe through the normally closed port and into the pathway 187. This occurs for a predetermined amount of time, as per the system controller's program control variables which can be set by the user.

Figure 8:
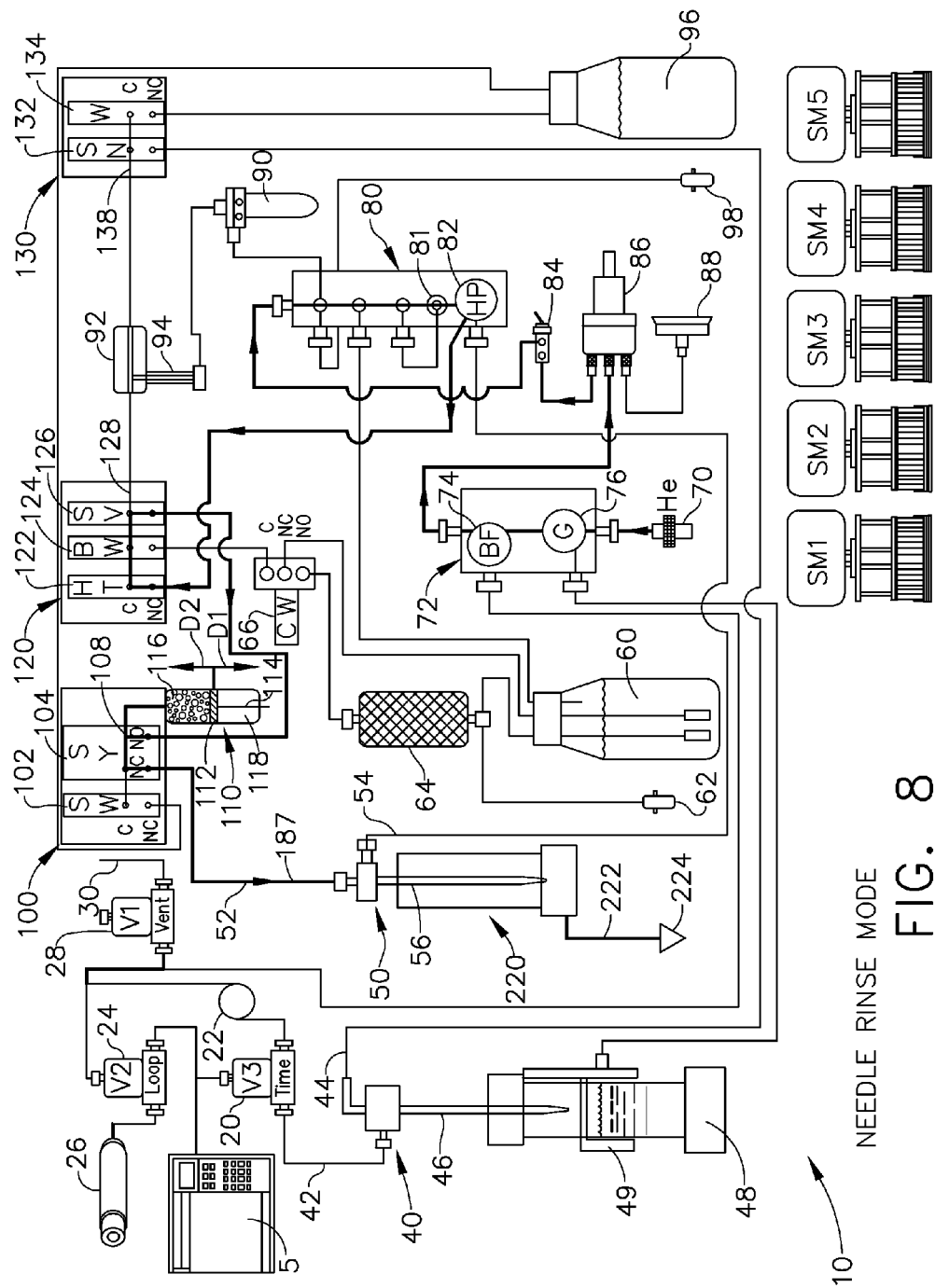
FIG. 8 is a fluidic schematic diagram of the automated headspace sampler system of FIG. 1, showing the system in an operating mode called "Needle Rinse."

Referring now to FIG. 8, the system 10 is now in a Needle Rinse Mode. The wash station 220 is still mounted to the second station over the sample needle 56. This time, instead of rinse water, helium gas is now run through the syringe in the same cyclic manner as was described in the previous Syringe Rinse Mode that was illustrated in FIG. 7. The helium gas is derived at the input 70, and runs through the helium manifold and the multi-port manifold 80, and to the mixing manifold 120. The HT and SD solenoids are turned on, so the helium runs through those two solenoids and out to the SY solenoids at its normally open port. The SY solenoid is turned off at this stage so that helium gas can be introduced into the upper displacement volume 116 while the plunger is moved downward in the D1 direction. Once the syringe is full, it will then have its plunger moved in the opposite direction D2 while the SY solenoid changes state so that the helium gas can move through its normally closed port into the pathway 187 to the wash station 220. This all occurs while the first vial 200 is still equilibrating.

Figure 9:
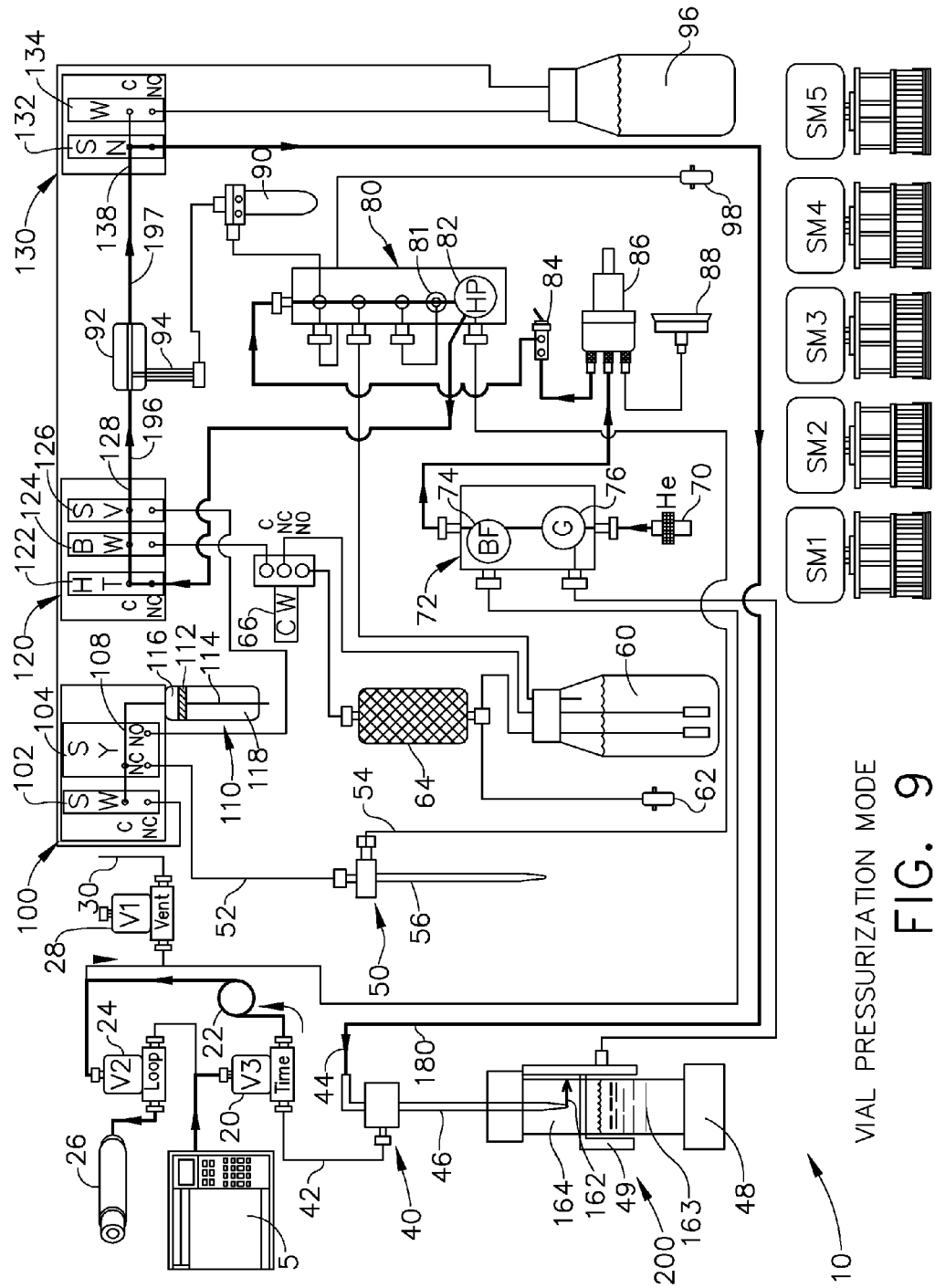
FIG. 9 is a fluidic schematic diagram of the automated headspace sampler system of FIG. 1, showing the system in an operating mode called "Vial Pressurization."

Referring now to FIG. 9, the system 10 is now in a Vial Pressurization Mode. In this mode of operation, the HT and SN solenoids are turned on. Helium gas flows from the helium input 70 through the helium manifold, the multi-port manifold 80, and the HT valve, and the mixing manifold 120, through the SN valve and down through the pathway 180 into the first vial headspace, which comes out the pathway 162 into the headspace 164. This action pressurizes the headspace 164 to a known minimum magnitude of pressure.

Figure 10:
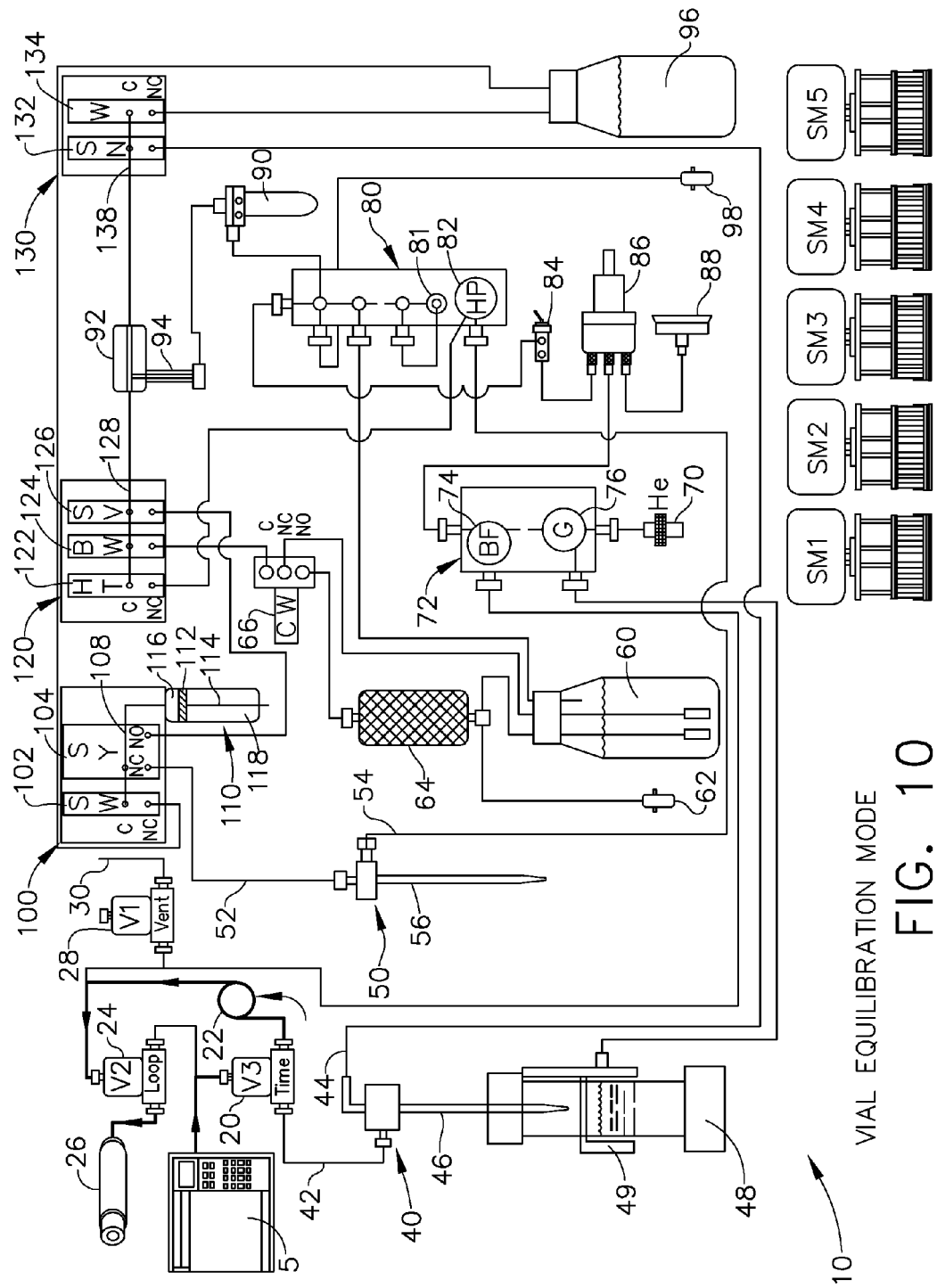
FIG. 10 is a fluidic schematic diagram of the automated headspace sampler system of FIG. 1, showing the system in an operating mode called "Vial Equilibration."

Referring now to FIG. 10, the system 10 is now in a Vial Equilibration Mode. All the solenoids are turned off at this step, and there is no gas flow except for the small amount of helium gas running into and out of the GC unit 5. The helium gas that was just added in a previous vial pressurization step is now equilibrating with the original headspace gasses in the headspace region 164.

Figure 11:
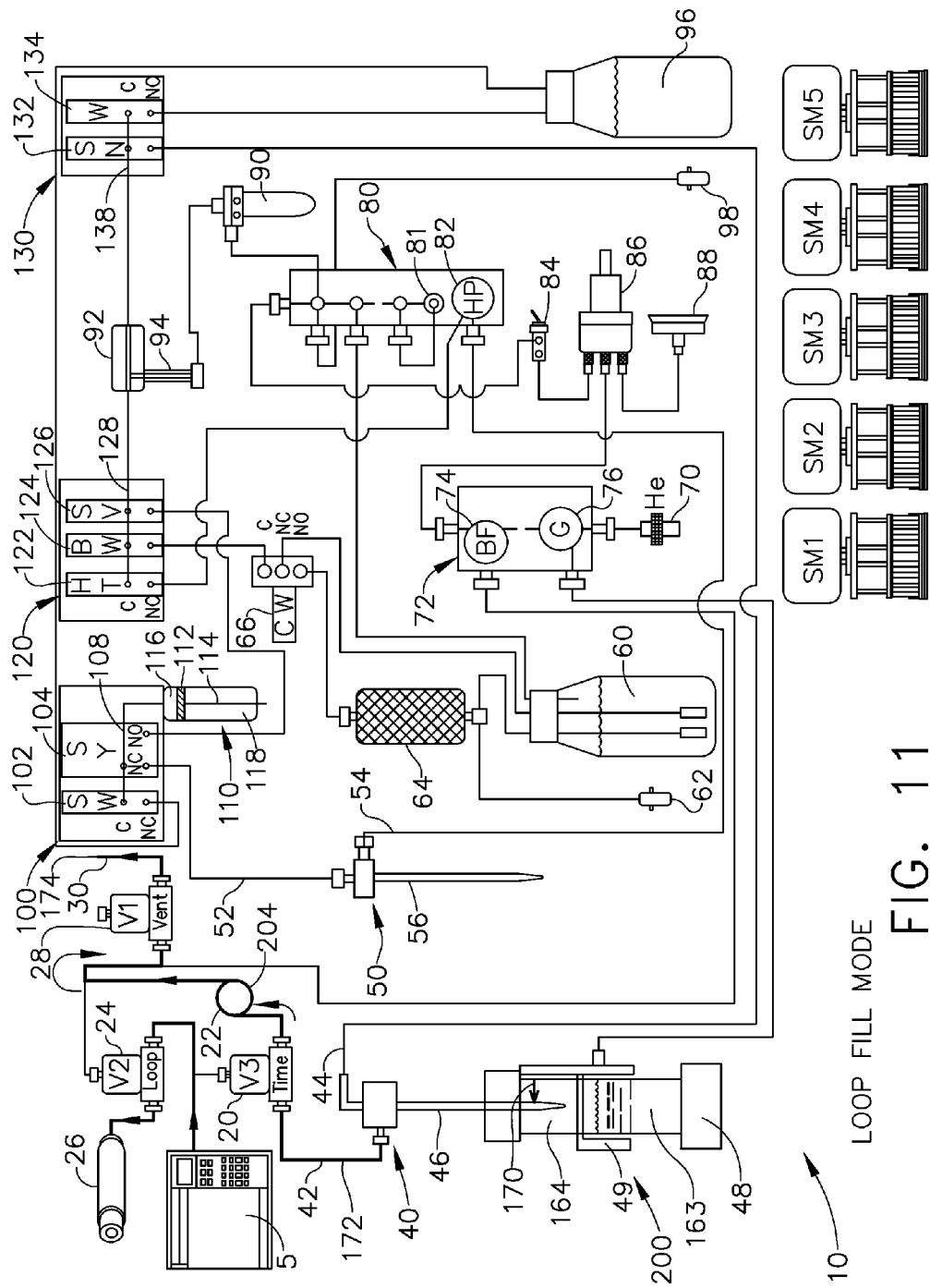
FIG. 11 is a fluidic schematic diagram of the automated headspace sampler system of FIG. 1, showing the system in an operating mode called "Loop Fill."

Referring now to FIG. 11, the device 10 is now in a Loop Fill Mode of operation so as to fill the sample loop 22. The solenoids V1, V2, and V3 are all turned on, and all the other solenoids in the system 10 are turned off. The pressure of the sample within the headspace 164 will cause some of the headspace gasses to move through the pathway 170 into the headspace needle 46 and out through the pathway 172 so that sample gas fills the loop 22 with sample gasses at 204. Some of these gasses will continue on through the solenoid V1 and out through the vent at 174.

Figure 12:
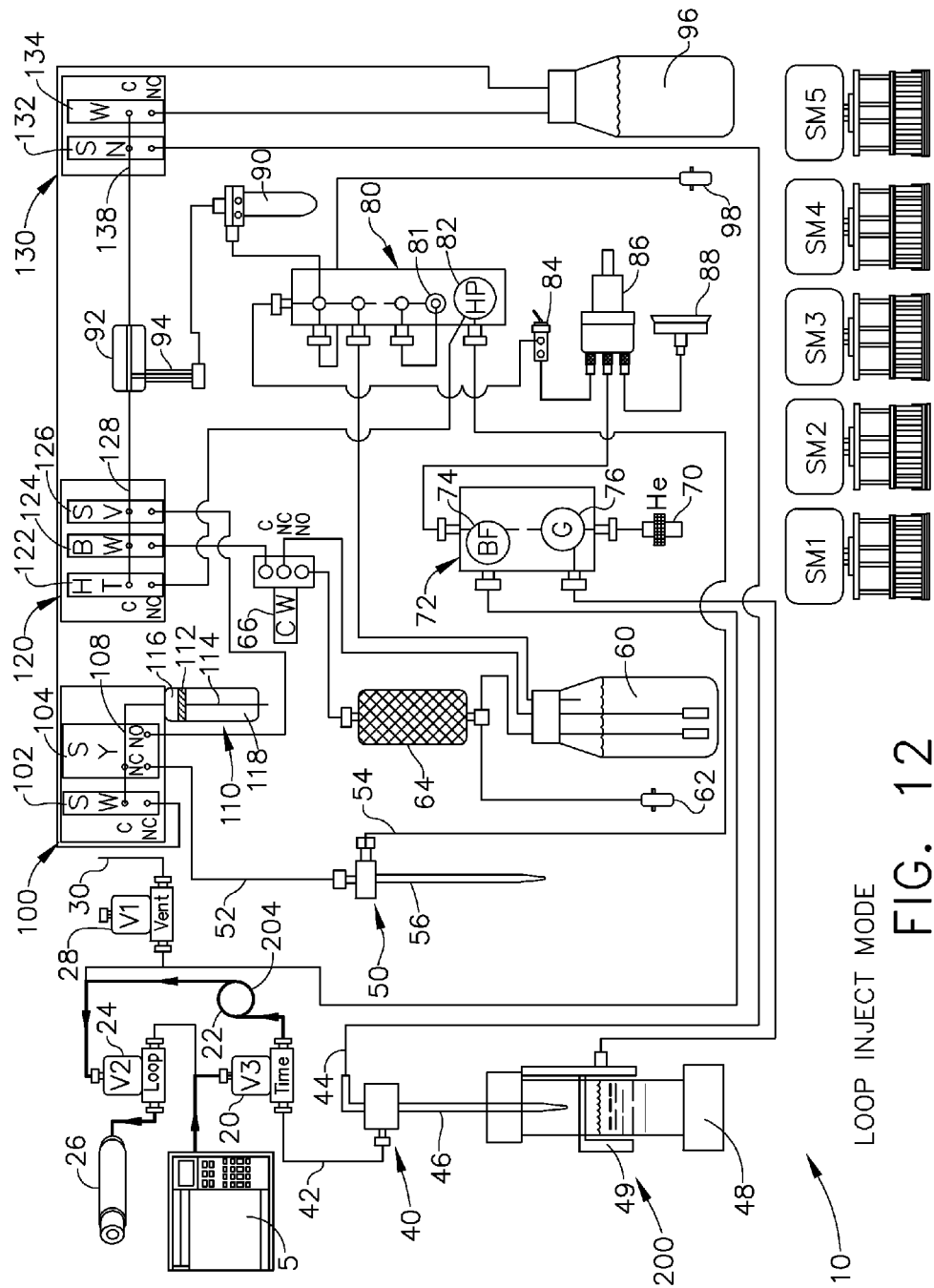
FIG. 12 is a fluidic schematic diagram of the automated headspace sampler system of FIG. 1, showing the system in an operating mode called "Loop Inject."

Referring now to FIG. 12, the system 10 is now in a Loop Inject Mode of operation. All of the solenoids are turned off, and the gaseous samples at 204 that are within the sample loop 22 are now moved through the heater 26 into the input of the GC device 5. The helium output of the GC instrument 5 is moved through the solenoid V3 and into the sample loop 22, which drives the sample gasses 204 back into the GC's input. This provides the GC with a known volume of sample gasses for analyzation purposes.

Figure 13:
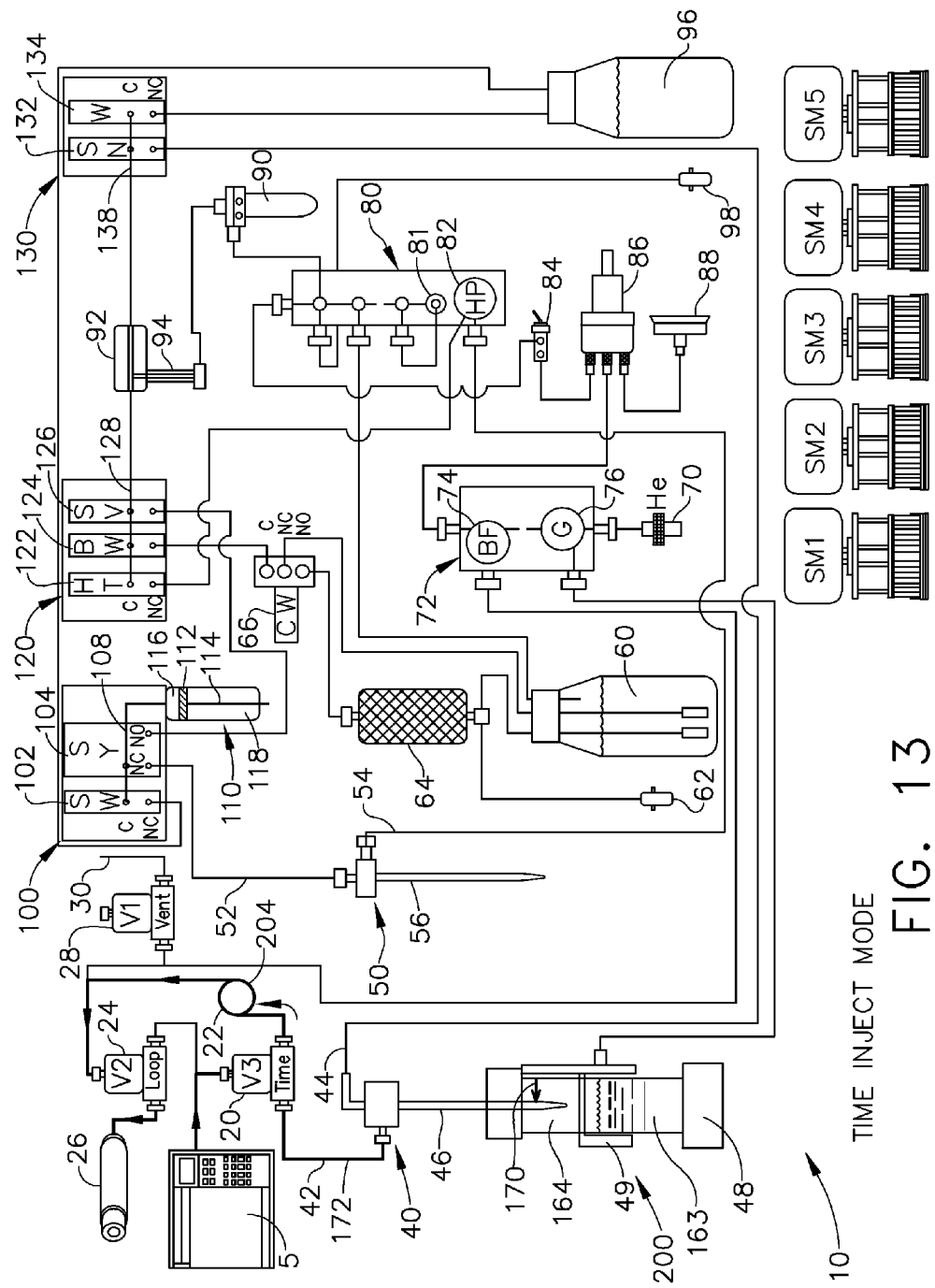
FIG. 13 is a fluidic schematic diagram of the automated headspace sampler system of FIG. 1, showing the system in an operating mode called "Time Inject."

Referring now to FIG. 13, the system 10 is now in a Time Inject Mode of operation. The solenoid V3 is turned on, and all other solenoids are turned off. The pressure in the headspace gasses 164 within the first vial 200 push the sample gasses through the pathway 172 and into the sample loop 22. The sample compound in the loop at 204 is then directed into the GC's input, through the heater 26. This occurs for a predetermined amount of time, under control of the system controller. This is all pre-programmed in advance, as determined by the system's user.

It will be understood that the system 10 could work with a single sampling station that contains a single dual-port needle (or alternatively, two single port needles) instead of the pair of sampling stations 40 and 50, although the system piping (i.e., the fluidic pathways) and control solenoids would have to be adjusted accordingly. In this alternative embodiment, the field sample vial (such as vial 210) would be first mounted onto the needle at the single sampling station and have a predetermined amount of liquid drawn from the vial and transferred into the displacement volume of the syringe. Then the field sample vial would be dismounted from the single sampling station, and an empty vial (i.e., a second vial) would then be mounted to that sampling station. The liquid in the syringe would then be transferred into that second vial. It should be noted, however, that the second vial will either become somewhat pressurized when the liquid sample is transferred into that second vial, or the inner spaces of the second vial will have to be placed under a vacuum before the liquid sample is transferred into the second vial. The use of a vacuum pump can accomplish the task of pulling a vacuum on the second vial, by drawing some of the gas from the initially empty vial, though the needle, the "vent" solenoid V1, and to the vacuum pump at 30. This vacuum pulling step on the second vial could take place while the field sample liquid (with the dissolved contaminants) is contained within the displacement volume of the syringe. (The system passageways would need to be somewhat revised to accommodate everything being directed to only one sampling station with a single dual-port needle subassembly, rather than the two samplings stations that are depicted on FIG. 1, for example.)

Figure 14:
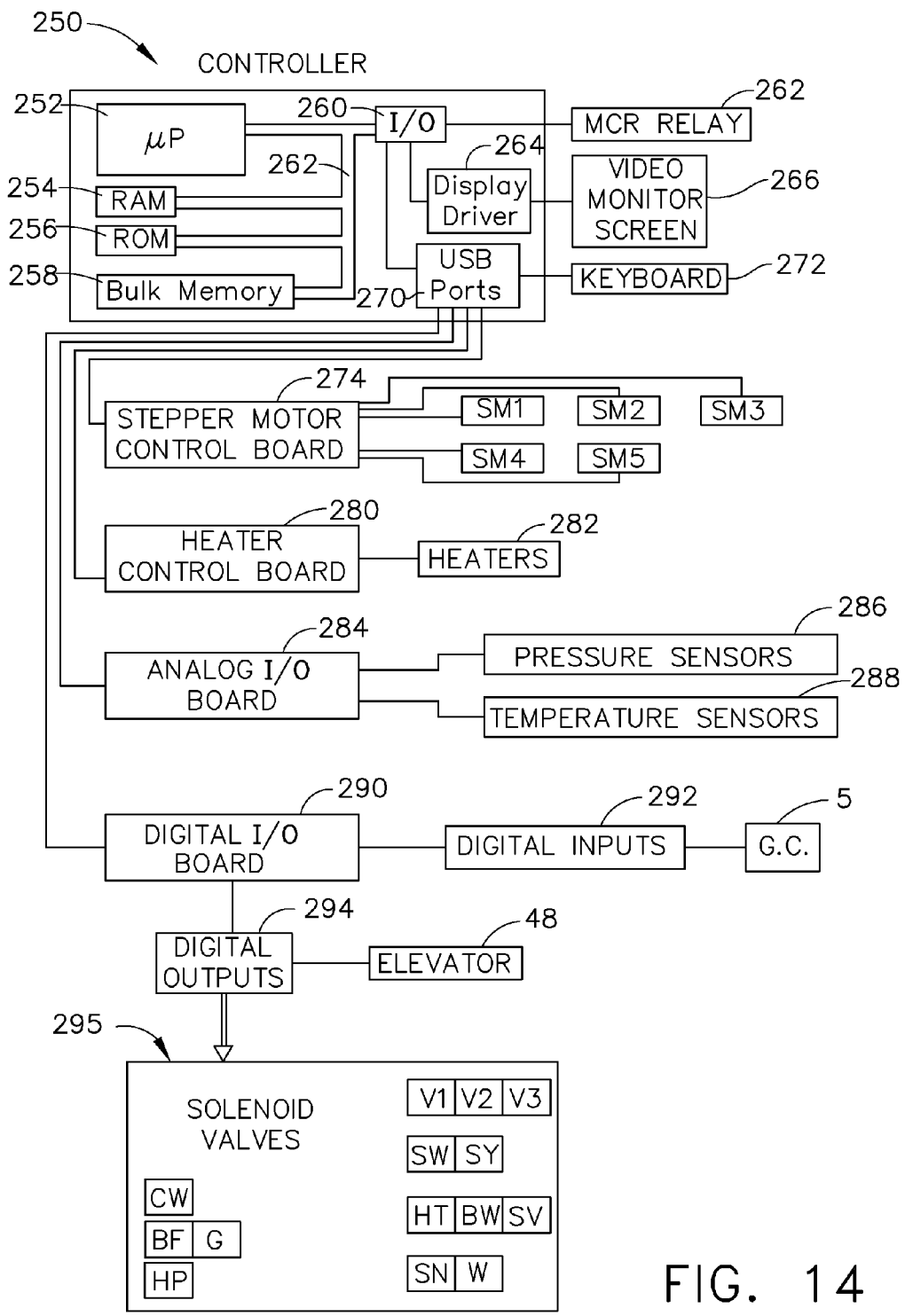
FIG. 14 is a block diagram illustrating some of the important components of the system, including a system controller and its various controlled devices and sensors.

Referring now to FIG. 14, a block diagram of the major electrical components is depicted, starting with a system controller that is generally designated by the reference numeral 250. A microprocessor or microcomputer 252 will execute programming instructions that will activate the appropriate controlled devices, and will receive input information during the execution of the computer program. The controller 250 may be implemented as a single-board computer if desired, and in any form would contain some Random Access Memory (RAM) 254, Read Only Memory (ROM) 256, and a bulk memory device 258, such as a hard disk drive or some type of optical storage memory. Typically there will be a system address and data bus 262 that will not only connect the microprocessor/microcomputer 252 to the memory elements, but also to input/output interface circuitry at 260.

The input/output (I/O) circuitry will communicate with all of the external control devices and input sensors. This will include a display driver circuit 264 and driver circuitry for multiple USB ports at 270. Display driver 264 will control a video monitor screen 266, which typically will be a flat panel display. USB ports 270 can communicate to a keyboard 272. Optionally, the monitor screen 266 can be a touch screen display, and in that situation, there may not be any keyboard at all, but instead, a virtual keyboard can appear on the touch screen display, if the system is programmed in that manner.

The I/O circuit 260 can also communicate to an MCR relay 262. Via the USB ports 270, the I/O 260 will communicate with other control boards that can be plugged into the main controller board, or can reside in separate enclosures, if desired. Examples of such control boards are a stepper motor control board 274, a heater control board 280, an analog I/O board 284, and a digital I/O board 290.

In the control system described for the device 10, the separate motor control board 274 will control the 5 stepper motors SM1, SM2, SM3, SM4, and SM5; the heater control board 280 will control the heaters 282, including the water heater 64 and the heater that is to heat the first sample vial 200; the analog I/O board 284 will receive signals from the pressure sensors 286 and temperature sensors 288; and the digital I/O board 290 will receive signals from digital inputs 292 and will send command signals to digital outputs 294.

One of the digital inputs is a "ready" signal that is sent by the GC device 5. There are many digital outputs, including one that controls the elevator 48, and digital outputs for each of the solenoid valves, which are grouped on FIG. 14 by the reference numeral 295. Each of the solenoid valves will require a separate digital output signal, so they can be controlled individually.

It will be understood that the block diagram of FIG. 14 is representative of a specific embodiment that is described herein, and the technology disclosed herein can be designed in many different forms, while still performing the functions that are required for this engineering application.

It will be understood that many of the logic operations used in the technology disclosed herein could be performed by "pneumatic logic" rather than electronic logic, if desired. For example, the electromechanical solenoids discussed above could be replaced by air-powered solenoids, using pneumatic-style control logic. Such pneumatic logic (or "air logic") would probably seem a step backward in time, and a microprocessor circuit might still be needed to provide control over certain mechanisms that simply would be unwieldy to implement with air logic. This is especially true for the stepper motor controls, which have now been developed to a very reliable form of precise movement control at a relatively inexpensive price. Moreover, a microprocessor circuit probably would still be needed to generate the displays for the monitor screen, and for sensing other inputs, such as temperature and pressure, although discrete analog and digital logic could be used for some of that.

Discussion of Flow Chart

Figure 15:
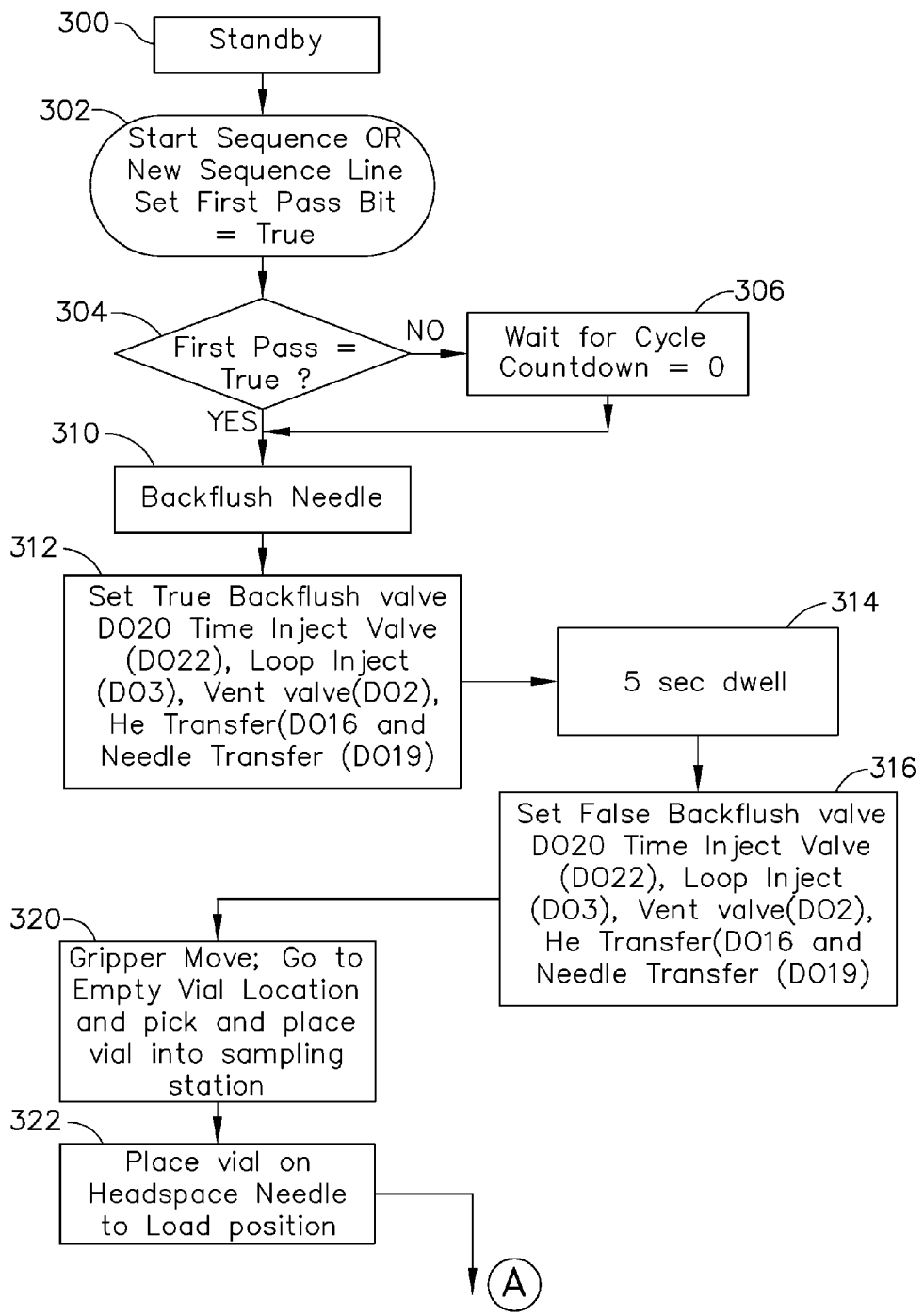
FIGS. 15-19 combined are a flow chart showing some of the logical steps used for controlling the various operating modes of the automated headspace sampler of the technology disclosed herein.
Figure 16:
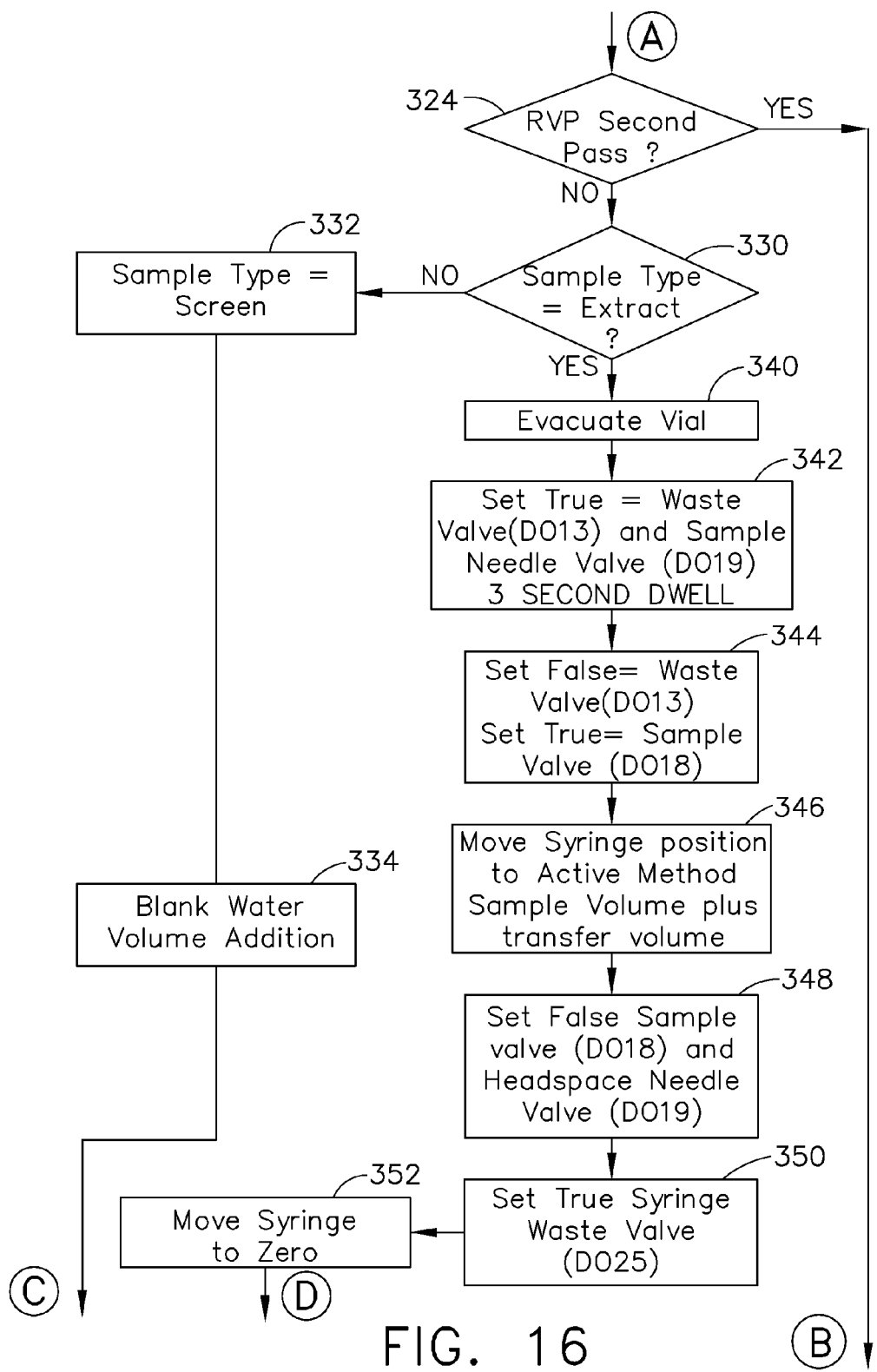
Figure 17:
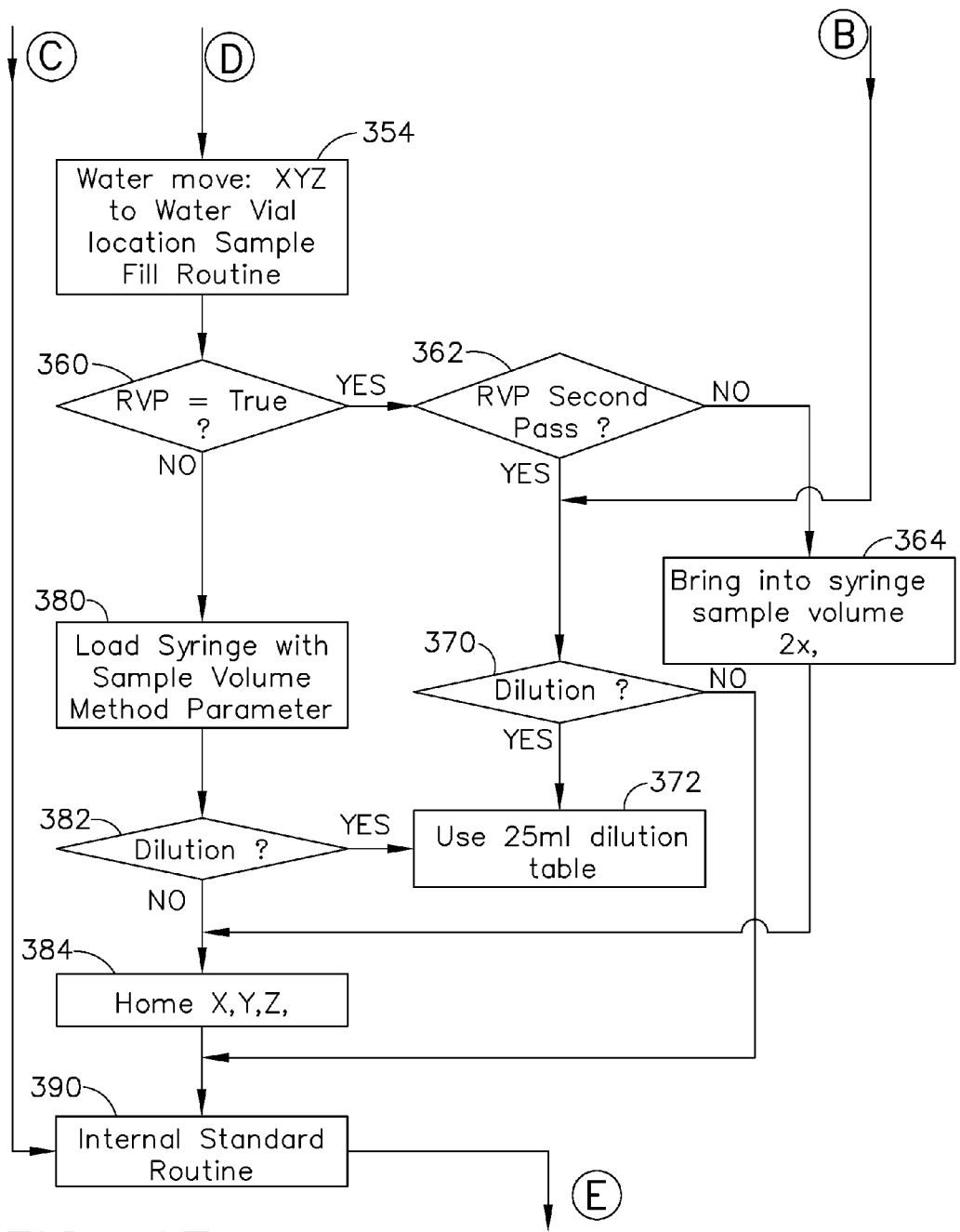
Figure 18:
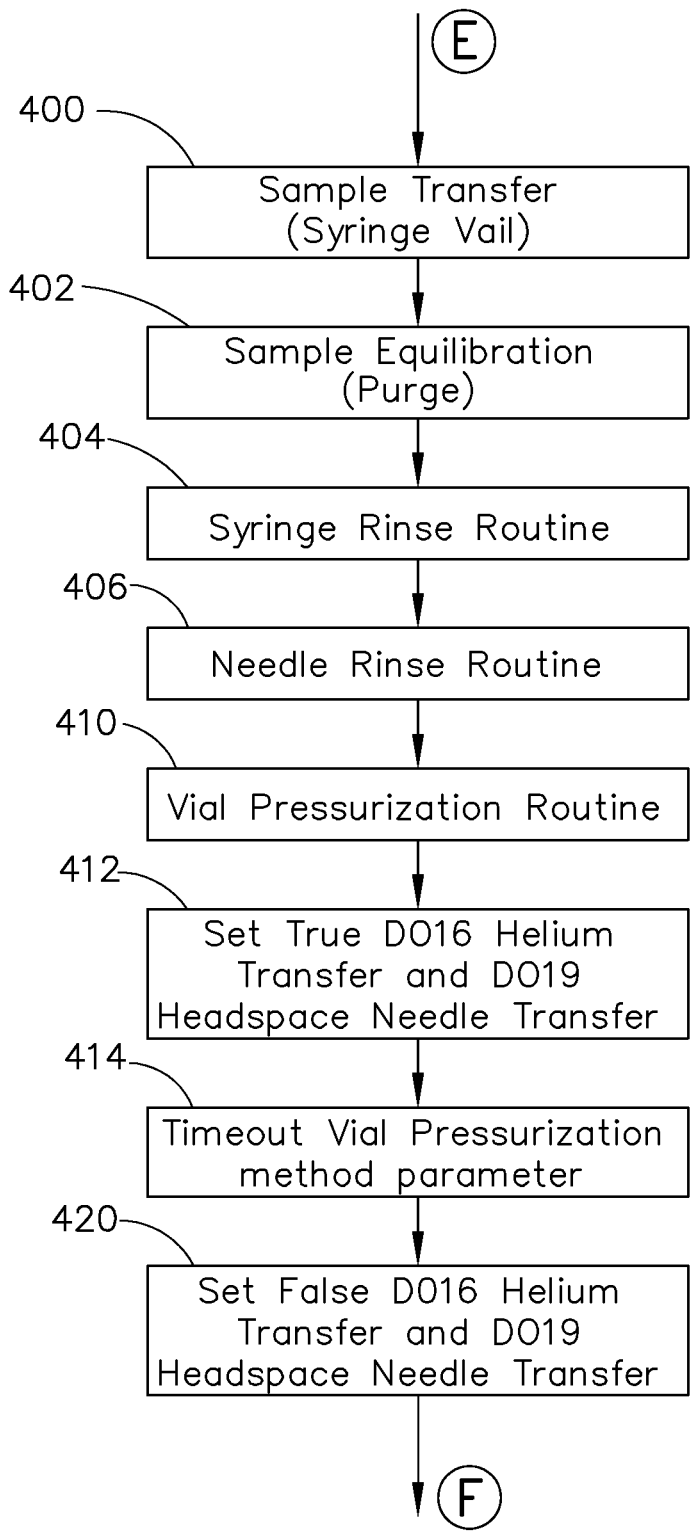
Figure 19:
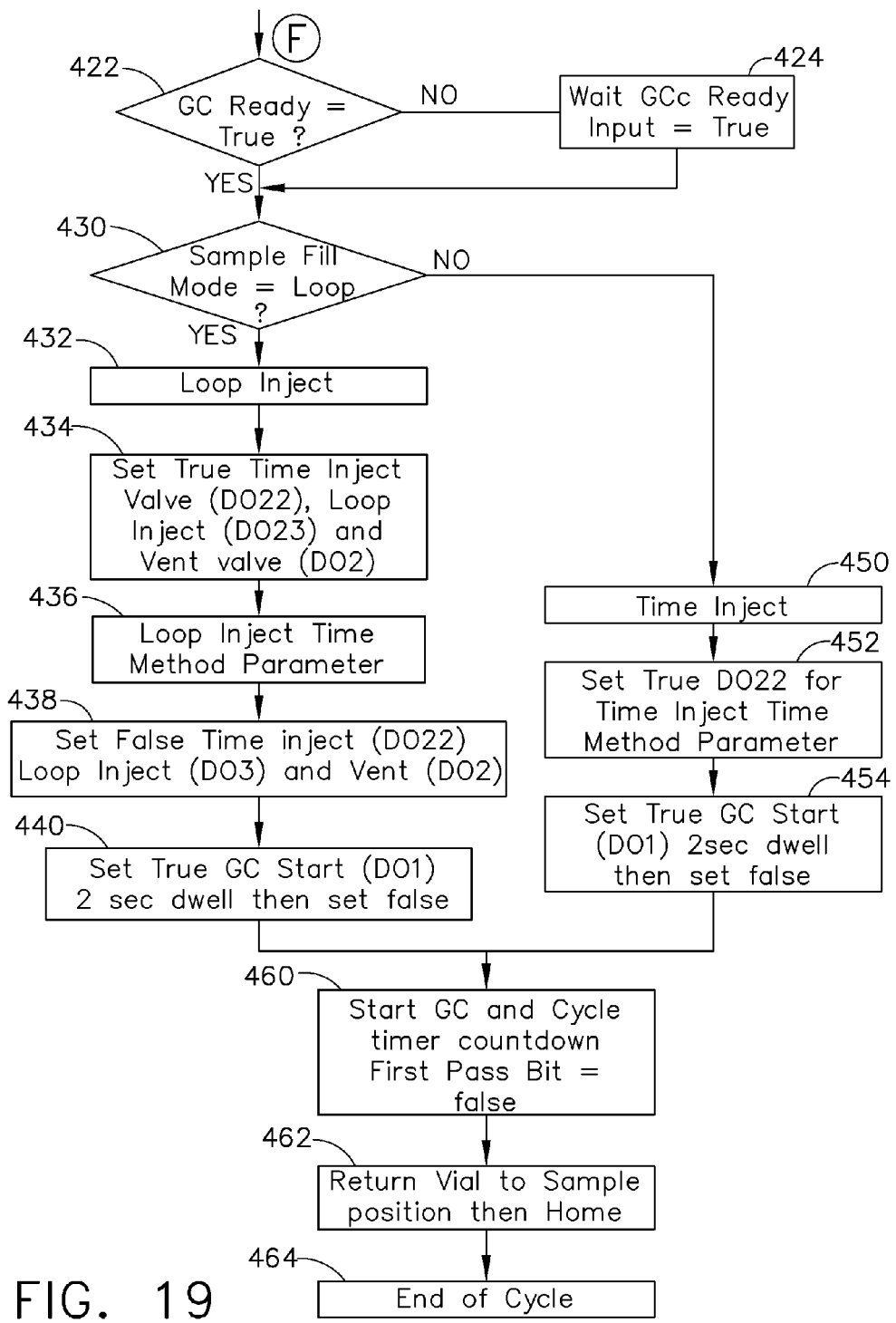

FIGS. 15-19 are a flow chart showing some of the important steps in an automatic controller routine for the technology disclosed herein. Referring now to FIG. 15, a "Standby" mode is shown as a step 300. The equipment of the device 10 is in the state as represented by FIG. 1 in the Standby mode. The next step 302 initiates a start sequence and sets a "first pass" bit to logic 1, or "true." The next step 304 is a decision step to determine if the "first pass" variable is equal to true, and if not (i.e., if it is at logic 0, or "false"), the logic flow is directed to a step 306 that waits for a cycle countdown. If the first pass variable was true, then the logic flow is directed to a step 310 which is a "backflush" step for back flushing the needle. This backflush step is represented on the equipment diagrams in FIG. 2.

In the Backflush Mode, several solenoids are turned on, and at a step 312 the controller turns on the backflush valve (solenoid BF), the time inject valve (solenoid V3), the loop inject valve (solenoid V2), the helium transfer valve (solenoid HT), and the needle transfer valve (solenoid SN). A step 314 now performs a 5 second time delay. After that occurs, a step 316 turns those same valves/solenoids back off, that were just turned on at step 312.

A step 320 now moves the gripper to a vial location having an empty vial and picks up and places that vial into the sampling station, which is the first station 40 on FIG. 1. A step 322 now places the empty vial onto the headspace needle 46 to a load position.

A decision step 324 now determines if an RTV second pass should be performed, and if the answer is YES, then the logic flow is directed to a decision step 370 where a dilution procedure might occur. If the answer was NO at step 324 then the logic flow is directed to a decision step 330 where it is determined if the sample type is "Extract," or "Screen.". If the answer is YES, then the logic flow is directed to a step 340 (for "Extract"). If the answer is NO, then the logic flow directed to a step 332 where the sample type is set to "Screen." If the sample type is "Screen," then a step 334 adds some blank water of a predetermined volume, and then the logic flow is directed to an Internal Standard routine at a step 390.

If the logic flow from step 330 is directed to step 340, where the vial is to be evacuated, this represents the state of the equipment as depicted on FIG. 3A, which is also referred to as the "Prevacuation Mode." In this mode, the vial has helium gas run through its headspace and the pathways, including the headspace needle 46. After that occurs for a predetermined time period (such as 13 seconds), then the logic flow is directed to a step 342 which is the first stage of an "Evacuation Mode." The "empty" first vial will now contain inert (e.g., helium) gas at atmospheric pressure, and it is ready for the next process steps that will ultimately load fluid into this first vial from a second vial which contains a field sample of fluid.

At step 342 the waste valve (solenoid W) and the needle valve (solenoid HT) are both turned on for a predetermined time period, such as three seconds or 5 seconds. This is illustrated on the system diagram drawing of FIG. 3B. A step 344 is now performed, which is referred to as the second stage of the Evacuation Mode. This is represented by the diagram of FIG. 3C. At this step, the waste valve (solenoid W) is turned off, and the sample valve (solenoid SV) is turned on. A step 346 now moves the plunger of the syringe downward to allow its upper displacement volume 116 to be evacuated with the clean helium gas that was previously moved into the first vial 200. After a predetermined time interval that is required to evacuate a predetermined volume from the first vial, a step 348 turns off the sample valve (solenoid SV) and turns off the headspace needle valve (solenoid SN).

The logic flow is now directed to a step 350, which is the beginning of the third stage of the "Evacuation Mode." The syringe waste valve (solenoid SW) is turned on, and at a step 352 the syringe plunger is moved upward to its zero position, and this causes the fluids inside the syringe displacement volume 116 to be moved down to the waste holding container 96.

The logic flow is now directed to a step 354, which is the beginning of the "Sample Fill Mode," in which the gripper is used to grab the field sample vial of interest, by controlling the X, Y, and Z axes stepper motors. This field sample vial is now moved to the second station, where it will be mounted on the sample needle 56. There are many sub-steps that occur at the beginning of the Sample Fill Mode, and the logic flow is directed to a decision step 360 to determine if the RPV variable is true, and if not, the logic flow is directed to a step 380. If RPV is true, then the logic flow is directed to a decision step 362 that determines whether or not this is an RPV second pass. If not, the logic flow is directed to a step 364 that brings into the syringe a sample volume 2X, and the logic flow is then directed to a step 384.

If the answer was YES at step 362, then the logic flow is directed to a decision step 370 to determine if there will be any dilution for this sample. If not, the logic flow is directed to a step 390. If there is dilution to be performed, the logic flow is directed to a step 372 that uses a dilution table that is stored in the memory of the controller. The logic flow is then directed to a step 384.

When the logic flow arrives at step 380, the syringe is loaded with the sample volume from the field sample vial 210 that is mounted to the sample needle 56. This is the water sample containing the dissolved contaminants that is within the second vial 210 that is mounted at the second station, which was just moved by the gripper under control of the three stepper motors. At step 380, the system will have the configuration as depicted on FIG. 4A. A decision step 382 now determines whether or not a dilution procedure will occur, and if the answer is YES, the logic flow will be directed to the step 372. If not, then the logic flow is directly moved to step 384, which homes the stepper motors in the three axes. The logic flow is now directed to an Internal Standard routine at a step 390. The configuration of the system at step 390 is depicted on FIG. 4B. A small amount of the internal standard compound will be injected by the internal standard solenoid (solenoid IS) and this compound is taken from the internal standard holding tank 90. This was described above in reference to FIG. 4B.

The logic flow is now directed to a step 400, which is the "Sample Transfer Mode" of operation, and was diagrammatically presented in FIG. 5. During this step, the plunger of the syringe is moved upward to empty the liquid sample from the syringe and move that liquid sample into the first vial 200 that is mounted on the headspace needle 46. Any internal standard compound in the passageways 128 and 138 will be included in this sample transfer into the first vial. After this step has been completed, the liquid sample that was in the second vial 210, which originally contained the field sample with the dissolved contaminants, has now been moved to the headspace needle first station 40, where those dissolved contaminants can be allowed to migrate into the headspace area 164, which is the vapor phase of the sample (as opposed to the contaminants when they were still dissolved in the liquid phase, which is at the portion 163 of the first vial).

The logic flow is now directed to a step 402, which is the "Sample Equilibration Mode," which allows the compounds of interest (in this case the dissolved contaminants) that are in the liquid phase to be partitioned into the gaseous ("vapor") phase of the headspace. The configuration of the system equipment in this sample equilibration is shown on FIG. 6. Since the sample equilibration phase will take some time, other operations can take place during that same time period.

A step 404 now executes the "Syringe Rinse Mode," and this stage of the equipment operation is diagrammatically depicted in FIG. 7. Rinse water is taken from the container 60 and run through the syringe and to a wash station 220. After that occurs, a step 406 performs a "Needle Rinse" routine, in which the equipment is diagrammatically presented in FIG. 8. Instead of rinse water, helium gas is run through the syringe, and is ultimately directed to the same wash station.

Once the two rinse routines are finished, and the Sample Equilibration routine is finished, the logic flow is now directed to a "Vial Pressurization" routine, and the equipment is now in the state that is diagrammatically depicted in FIG. 9. After entering this routine at step 410, a step 412 turns on the helium transfer valve and the headspace needle valve (solenoids HT and SN). A step 414 performs a vial pressurization timeout. This routine pressurizes the headspace to a known minimum pressure.

After the Vial Pressurization Mode is complete, the logic flow arrives at a step 420 which is a "Vial Equilibration" step. The helium transfer and headspace needle transfer valve (solenoids HT and SN) are turned off, and the vial equilibrates. The state of the equipment at this stage is depicted on FIG. 10. After that has occurred for a predetermined amount of time, which can be set by the user using the system controller setpoints, the logic flow is directed to a decision step 422 that determines whether or not the GC is ready to receive its next sample. If not, a step 424 waits until the GC is ready, by reading the "GC Ready" input. Once that is true, the logic flow is directed to a decision step 430.

Decision step 430 determines whether or not the Sample Fill Mode will be a loop inject or a time inject. In either case, the gasses in the headspace 164 will be directed into the sample loop 22, so that the headspace gasses now become the sample 204 within the sample loop. The three solenoid valves V1, V2, and V3 are all on, and the sample loop is filled with an aliquot of headspace gasses, some of which are allowed to travel out through the vent at 174. This mode is fairly quick, because there are not unlimited headspace gasses to fill the loop and then be vented.

If the decision at step 430 was for a loop inject, the logic flow is directed to a step 432 to begin that mode. At a step 434, the three solenoid valves V1, V2, and V3 are turned on, so that an aliquot of headspace gasses from the first vial 200 are injected into the sample loop 22 and on through to the vent at 174. This fills the sample loop 22 with the sample headspace gasses 204. The state of the equipment at this stage is depicted on FIG. 11, which is the "Loop Fill Mode."

A step 436 now begins a loop inject time method parameter, and a step 438 turns off the three solenoid valves V1, V2, and V3. This is the "Loop Inject Mode," and the state of the equipment in this mode is depicted on FIG. 12. A step 440 sets true the GC Start digital output, for approximately two second dwell time, and then that output is turned off. This will transfer the appropriate volume of sample gasses 204 from the sample loop 22 through the heater 26, and into the input of the GC.

If the decision at step 430 was for a time inject procedure, then the logic flow is directed to a step 450, which is the beginning of the "Time Inject Mode," and the equipment state during that mode is depicted on FIG. 13. A step 452 turns on the time inject valve, which is solenoid V3. A step 454 turns on the GC start digital output for approximately two seconds dwell time, and then turns that output back off. That's the end of the time inject procedure, and the exact amount of time during which the inject will take place during step 454 is determined by the system controller. This is a parameter that can be controlled by the user, although a standard amount of time is typically built into the system as a default setting.

The logic flow from both the time inject and loop inject modes is now directed to a step 460 that starts the GC and cycle timer countdown, and a "first pass bit" is set to FALSE. A step 462 returns the vial to the headspace position, and then to home. A step 464 is the end of the sampling cycle for this particular set of vials.

It will be understood that the logical operations described in relation to the flow charts of FIGS. 15-19 can be implemented using sequential logic (such as by using microprocessor technology), or using a logic state machine, or perhaps by discrete logic; it even could be implemented using parallel processors. One preferred embodiment may use a microprocessor or microcontroller (e.g., microprocessor 252) to execute software instructions that are stored in memory cells within an ASIC. In fact, the entire microprocessor 252, along with RAM and executable ROM, may be contained within a single ASIC, in one mode of the technology disclosed herein. Of course, other types of circuitry could be used to implement these logical operations depicted in the drawings without departing from the principles of the technology disclosed herein. In any event, some type of processing circuit will be provided, whether it is based on a microprocessor, a logic state machine, by using discrete logic elements to accomplish these tasks, or perhaps by a type of computation device not yet invented; moreover, some type of memory circuit will be provided, whether it is based on typical RAM chips, EEROM chips (including Flash memory), by using discrete logic elements to store data and other operating information (such as the control/operating variables stored, for example, in memory elements 254 and 256), or perhaps by a type of memory device not yet invented.

It will also be understood that the precise logical operations depicted in the flow charts of FIGS. 15-19, and discussed above, could be somewhat modified to perform similar, although not exact, functions without departing from the principles of the technology disclosed herein. The exact nature of some of the decision steps and other commands in these flow charts are directed toward specific future models of an EST Centurion-type automated sampler system, for example (see below), and certainly similar, but somewhat different, steps could be taken for use with other models or brands of automated sampler systems in many instances, with the overall inventive results still being the same.

It will be further understood that some of the terminology used herein can have alternative wording, while having the same or a similar meaning. For example, fluidic "pathways" and fluidic "passageways" essentially mean the same thing. A "port" and an "inlet" essentially mean the same thing, and a "port" or an "outlet" essentially mean the same thing; the word "port" is a general word that does not need to be restricted to something having a specific shape, or need to "aim" a fluidic flow in any particular manner or have the fluidic flow in a particular direction. In many of the pathways, and at many of the ports, the fluidic flow can be bidirectional, mainly depending on which operating mode the system is in at that moment. The words operating "mode," or "step," or "stage," or "routine" all have similar meanings. The terms "headspace," "headspace gasses," and "headspace region vapor" all have a similar meaning—they relate to the gaseous contents within a portion of a vial that also contains some liquid (or solid) in a different portion of that vial, and in most instances, there is no physical barrier between those two portions. Often (especially after equilibrating) there are similar chemicals in both portions; such sealed vials will typically contain sample materials (chemicals) both in a liquid (matrix) phase and in a vapor (or gas) phase, and the vial's headspace volume (or vial portion) includes the vapor phase contents.

The principles of the technology disclosed herein will soon be embodied in an automated sampling device that will be sold by EST Analytical, Inc. of Fairfield, Ohio, under the model number LGX 50.

As used herein, the word "dissolved" applies to gasses, liquids, and/or solids that are either mixed together, or are in solution together. In other words, if two liquids are mixed together in a single container (such as a vial), the word "dissolved" applies to that situation (even if such a combination would otherwise be called a "mixture"); if there are gasses in solution with a liquid, or solids in solution with a liquid, the word "dissolved" also applies to that situation. In many of the applications for the technology disclosed herein, the compound of interest will be considered a "contaminant," and that contaminant, whether in solid, liquid, or gaseous form, will typically be dissolved in a liquid at the outset of the sampling procedure.

As used herein, the word "partitioned" applies to the situation where a compound of interest (e.g., a contaminant) begins in solution, or mixed, with a liquid (such as water) and contained in a sealed vial, and that vial is induced (in some form) to have its liquid phase "transform" (i.e., partition) into a gas (or vapor) phase, in the headspace of the sealed vial. The inducement could be in the form, for example, of heating the vial, or mixing (stirring) the contents of the vial, or simply allowing the vial to equilibrate over time. This terminology is well-known in the field of headspace sampling.

As used herein, the term "proximal" can have a meaning of closely positioning one physical object with a second physical object, such that the two objects are perhaps adjacent to one another, although it is not necessarily required that there be no third object positioned therebetween. In the technology disclosed herein, there may be instances in which a "male locating structure" is to be positioned "proximal" to a "female locating structure." In general, this could mean that the two male and female structures are to be physically abutting one another, or this could mean that they are "mated" to one another by way of a particular size and shape that essentially keeps one structure oriented in a predetermined direction and at an X-Y (e.g., horizontal and vertical) position with respect to one another, regardless as to whether the two male and female structures actually touch one another along a continuous surface. Or, two structures of any size and shape (whether male, female, or otherwise in shape) may be located somewhat near one another, regardless if they physically abut one another or not; such a relationship could still be termed "proximal." Or, two or more possible locations for a particular point can be specified in relation to a precise attribute of a physical object, such as being "near" or "at" the end of a stick; all of those possible near/at locations could be deemed "proximal" to the end of that stick. Moreover, the term "proximal" can also have a meaning that relates strictly to a single object, in which the single object may have two ends, and the "distal end" is the end that is positioned somewhat farther away from a subject point (or area) of reference, and the "proximal end" is the other end, which would be positioned somewhat closer to that same subject point (or area) of reference.

It will be understood that the various components that are described and/or illustrated herein can be fabricated in various ways, including in multiple parts or as a unitary part for each of these components, without departing from the principles of the technology disclosed herein. For example, a component that is included as a recited element of a claim hereinbelow may be fabricated as a unitary part; or that component may be fabricated as a combined structure of several individual parts that are assembled together. But that "multi-part component" will still fall within the scope of the claimed, recited element for infringement purposes of claim interpretation, even if it appears that the claimed, recited element is described and illustrated herein only as a unitary structure.

All documents cited in the Background and in the Detailed Description are, in relevant part, incorporated herein by reference; the citation of any document is not to be construed as an admission that it is prior art with respect to the technology disclosed herein.

The foregoing description of a preferred embodiment has been presented for purposes of illustration and description. It is not intended to be exhaustive or to limit the technology disclosed herein to the precise form disclosed, and the technology disclosed herein may be further modified within the spirit and scope of this disclosure. Any examples described or illustrated herein are intended as non-limiting examples, and many modifications or variations of the examples, or of the preferred embodiment(s), are possible in light of the above teachings, without departing from the spirit and scope of the technology disclosed herein. The embodiment(s) was chosen and described in order to illustrate the principles of the technology disclosed herein and its practical application to thereby enable one of ordinary skill in the art to utilize the technology disclosed herein in various embodiments and with various modifications as are suited to particular uses contemplated. This application is therefore intended to cover any variations, uses, or adaptations of the technology disclosed herein using its general principles. Further, this application is intended to cover such departures from the present disclosure as come within known or customary practice in the art to which this technology disclosed herein pertains and which fall within the limits of the appended claims.

What is claimed is:

1. A method for sampling dissolved contaminants in liquid, said method comprising:
   (a) providing a sampling system, having:
      (i) a first vial having a first seal, said first vial containing a first gas;
      (ii) a first needle subassembly having a first port and a second port proximal to a distal tip;
      (iii) a second vial having a second seal, said second vial being substantially filled with a liquid sample that contains dissolved contaminants;
      (iv) a second needle subassembly having a third port and a fourth port proximal to a distal tip;
      (v) a syringe having a movable plunger, said syringe having a displacement volume that is bounded by said movable plunger and by an outer wall of said syringe;
      (vi) a source of gas pressure;
      (vii) a waste outlet;
      (viii) a sample outlet;
      (ix) a plurality of fluidic passageways between said first port of the first needle subassembly, said second port of the first needle subassembly, said third port of the second needle subassembly, said fourth port of the second needle subassembly, said source of gas pressure, said displacement volume of the syringe, said sample outlet, and said waste outlet;
      (x) a plurality of automatically controlled valves that are in communication with said plurality of fluidic passageways and which, for a predetermined operating mode, establish at least one fluidic pathway of said plurality of fluidic passageways; and
      (xi) a system controller that determines one of said predetermined operating modes for controlling said plurality of automatically controlled valves;
   (b) using said first needle subassembly, piercing said first seal of said first vial;
   (c) using said movable plunger of the syringe, drawing a predetermined first volume of said first gas from said first vial, and evacuating said first volume of the first gas to said waste outlet, thereby establishing a partial vacuum condition inside said first vial;
   (d) using said second needle subassembly, piercing said second seal of said second vial;
   (e) using said movable plunger of the syringe, drawing a predetermined second volume of said liquid sample with dissolved contaminants from said second vial, and transferring said second volume of the liquid sample with dissolved contaminants into said first vial, wherein said first volume is substantially equal to said second volume, so that contents of said first vial now are not substantially under pressure or under vacuum conditions;
   (f) partitioning said liquid sample with dissolved contaminants into a headspace region of said first vial, thereby allowing at least a portion of said dissolved contaminants to enter said headspace region as headspace region vapor; and
   (g) transferring an aliquot of said headspace region vapor to said sample outlet.

2. The method of claim 1, wherein said second vial contains a field sample.

3. The method of claim 1, wherein at least one of said first needle subassembly and said second needle subassembly comprises one of: (a) a dual-port concentric needle; and (b) a dual-port non-concentric needle; and (c) two single port needles.

4. The method of claim 1, further comprising a step of:
   substantially evacuating said first gas from said first vial by sweeping an interior volume of said first vial with an inert gas, before step (c) of claim 1.

5. The method of claim 1, further comprising the step of: equilibrating said liquid sample with dissolved contaminants in said first vial, during step (f) of claim 1.

6. The method of claim 1, wherein said source of gas pressure provides the impetus to displace said second volume of the liquid sample with dissolved contaminants from said second vial, in step (e) of claim 1.

7. The method of claim 1, wherein step (e) comprises:
   (i) during a first mode of operation, increasing said displacement volume by moving said plunger of the syringe in a first direction, thereby drawing said second volume of the liquid sample with dissolved contaminants from the second vial into said syringe;
   (ii) using said system controller, switching at least one of said plurality of automatically controlled valves to a different logic state, to enter a second mode of operation; and
   (iii) during said second mode of operation, decreasing said displacement volume by moving said plunger of the syringe in a second direction that is opposite to said first direction, thereby transferring said second volume of the liquid sample with dissolved contaminants from said syringe and into said first vial.

8. The method of claim 7, wherein: a position of said plunger is automatically controlled by a stepper motor, which receives control signals from said system controller.

9. The method of claim 1, wherein:
   (a) said first vial is selected by a gripper from a plurality of empty vials positioned on a tray, and
   (b) a position of said gripper is automatically controlled by a plurality of stepper motors, which receive control signals from said system controller.

10. The method of claim 1, wherein said liquid sample with dissolved contaminants substantially comprises: water with at least one of: (a) dissolved natural gas, (b) dissolved methane, (c) dissolved ethylene, and (d) dissolved ethane.

11. A method for sampling liquids, said method comprising:
    (a) providing a sampling system, having:
       (i) a first vial having a first seal, said first vial containing a first gas;
       (ii) a first needle subassembly having a first port and a second port proximal to a distal tip;
       (iii) a second vial having a second seal, said second vial being substantially filled with a liquid sample;

(iv) a second needle subassembly having a third port and a fourth port proximal to a distal tip;

(v) a syringe having a movable plunger, said syringe having a displacement volume that is bounded by said movable plunger and by an outer wall of said syringe;

(vi) a source of gas pressure;

(vii) a waste outlet;

(viii) a sample outlet;

(ix) a plurality of fluidic passageways between said first port of the first needle subassembly, said second port of the first needle subassembly, said third port of the second needle subassembly, said fourth port of the second needle subassembly, said source of gas pressure, said displacement volume of the syringe, said sample outlet, and said waste outlet;

(x) a plurality of automatically controlled valves that are in communication with said plurality of fluidic passageways and which, for a predetermined operating mode, establish at least one fluidic pathway of said plurality of fluidic passageways; and (xi) a system controller that determines one of said predetermined operating modes for controlling said plurality of automatically controlled valves;

(b) placing said first vial in a first position at said sampling system;

(c) using said first needle subassembly, piercing said first seal of said first vial;

(d) maintaining a sample integrity at said first seal by holding both said first needle subassembly and said first vial in their relative positions until after step (m) is completed;

(e) using said movable plunger of the syringe, drawing a first volume of said first gas from said first vial, thereby establishing a partial vacuum condition inside said first vial;

(f) using said movable plunger of the syringe, evacuating said first volume of the first gas to said waste outlet;

(g) placing said second vial in a second position at said sampling system;

(h) using said second needle subassembly, piercing said second seal of said second vial;

(i) maintaining a sample integrity at said second seal by holding both said second needle subassembly and said second vial in their relative positions until after step (j) is completed;

(j) using said movable plunger of the syringe, drawing a second volume of said liquid sample from said second vial;

(k) using said movable plunger of the syringe, transferring said second volume of the liquid sample into said first vial;

(l) partitioning said liquid sample into a headspace region of said first vial, thereby allowing at least a portion of said liquid sample to enter said headspace region as headspace region vapor; and (m) transferring an aliquot of said headspace region vapor to said sample outlet.

12. The method of claim 11, wherein said second vial contains a field sample.

13. The method of claim 11, wherein at least one of said first needle subassembly and said second needle subassembly comprises one of: (a) a dual-port concentric needle; and (b) a dual-port non-concentric needle; and (c) two single port needles.

14. The method of claim 11, wherein said liquid sample contains dissolved gasses, at least some of which are partitioned into said headspace region as headspace region vapor in step (l) of claim 11.

15. The method of claim 14, wherein said liquid sample with dissolved gasses substantially comprises: water with at least one of: (a) dissolved natural gas, (b) dissolved methane gas, (c) dissolved ethylene gas, and (d) dissolved ethane gas.

16. The method of claim 14, wherein said dissolved gasses within said liquid sample are not lost to atmosphere during the sampling process of steps (a) through (m), because:

(i) said first seal of the first vial is not pierced more than once during said sampling process;

(ii) said second seal of the second vial is not removed during said sampling process; and (iii) said second seal of the second vial is not pierced more than once during said sampling process.

17. The method of claim 14, wherein said dissolved gasses within said liquid sample are not exposed to outside contaminants during the sampling process of steps (a) through (m), because:

(i) said first seal of the first vial is not pierced more than once during said sampling process;

(ii) said second seal of the second vial is not removed during said sampling process; and (iii) said second seal of the second vial is not pierced more than once during said sampling process.

18. The method of claim 11, wherein said liquid sample contains at least one volatile organic compound (VOC), at least some of which is partitioned into said headspace region as headspace region vapor in step (l) of claim 11.

19. A method for sampling dissolved contaminants in liquid, said method comprising:

(a) providing a sampling system, having:

(i) a first vial having a first seal, said first vial containing a first gas;

(ii) a first needle subassembly having a first port and a second port proximal to a distal tip;

(iii) a second vial having a second seal, said second vial being substantially filled with a liquid sample that contains dissolved contaminants;

(iv) a second needle subassembly having a third port and a fourth port proximal to a distal tip;

(v) a syringe having a movable plunger, said syringe having a displacement volume that is bounded by said movable plunger and by an outer wall of said syringe;

(vi) a source of gas pressure;

(vii) a waste outlet;

(viii) a sample outlet;

(ix) a container that holds an internal standard compound;

(x) a plurality of fluidic passageways between said first port of the first needle subassembly, said second port of the first needle subassembly, said third port of the second needle subassembly, said fourth port of the second needle subassembly, said source of gas pressure, said displacement volume of the syringe, said sample outlet, said waste outlet, and said container holding an internal standard compound;

(xi) a plurality of automatically controlled valves that are in communication with said plurality of fluidic passageways and which, for a predetermined operating mode, establish at least one fluidic pathway of said plurality of fluidic passageways; and (xii) a system controller that determines one of said predetermined operating modes for controlling said plurality of automatically controlled valves;

(b) using said first needle subassembly, piercing said first seal of said first vial;

(c) using said movable plunger of the syringe, drawing a first volume of said first gas from said first vial, thereby establishing a partial vacuum condition inside said first vial;

(d) using said movable plunger of the syringe, evacuating said first volume of the first gas to said waste outlet;

(e) using said second needle subassembly, piercing said second seal of said second vial;

(f) using said movable plunger of the syringe, drawing a second volume of said liquid sample with dissolved contaminants from said second vial and into said displacement volume of the syringe;

(g) using one of said plurality of automatically controlled valves, injected a third volume of said internal standard compound from said container into at least one of said plurality of fluidic passageways;

(h) using said movable plunger of the syringe, transferring said second volume of the liquid sample with dissolved contaminants, along with said third volume of the internal standard compound, into said first vial;

(i) partitioning said liquid sample with dissolved contaminants, and said internal standard compound, into a headspace region of said first vial, thereby allowing at least a portion of said dissolved contaminants and said internal standard compound to enter said headspace region as headspace region vapor; and (j) transferring an aliquot of said headspace region vapor and said internal standard compound to said sample outlet.

20. The method of claim 19, wherein said third volume is a predetermined amount of said internal standard compound, under the control of a user-selected value that is entered into a processing circuit with a memory circuit, of said system controller.

21. The method of claim 19, wherein said liquid sample with dissolved contaminants substantially comprises: water with at least one of: (a) dissolved natural gas, (b) dissolved methane, (c) dissolved ethylene, and (d) dissolved ethane.

\* \* \* \* \*